(12) United States Patent
Gramnas

(10) Patent No.: US 6,572,658 B1
(45) Date of Patent: *Jun. 3, 2003

(54) KNEE PROSTHESIS

(75) Inventor: Finn Gramnas, Kinna (SE)

(73) Assignee: Gramtec Innovations AB, Kinna (SE)

( * ) Notice: Subject to any disclaimer, the term of this patent is extended or adjusted under 35 U.S.C. 154(b) by 12 days.

This patent is subject to a terminal disclaimer.

(21) Appl. No.: 09/667,052

(22) Filed: Sep. 20, 2000

Related U.S. Application Data

(63) Continuation-in-part of application No. 09/250,577, filed on Feb. 16, 1999, now Pat. No. 6,159,248.
(60) Provisional application No. 60/083,318, filed on Apr. 28, 1998.

(30) Foreign Application Priority Data

Jul. 13, 1998 (SE) ............................... 9802515

(51) Int. Cl.$^7$ ............................... A61F 2/64; A61F 2/68
(52) U.S. Cl. ....................................... 623/44
(58) Field of Search ..................... 623/41–45

(56) References Cited

U.S. PATENT DOCUMENTS 3,982,279 A * 9/1976 Valenti et al. .................. 3/27
4,206,519 A 6/1980 Blatchford et al. ............... 3/27
4,351,070 A 9/1982 Blatchford ........................ 3/27
6,159,248 A * 12/2000 Gramnas ....................... 623/44

FOREIGN PATENT DOCUMENTS

WO WO 97/10781 3/1997 ............. A61F/2/64

* cited by examiner

Primary Examiner—Bruce Snow
(74) Attorney, Agent, or Firm—Gardner Carton & Douglas LLC

(57) ABSTRACT

A knee prosthesis comprising two pivotally interconnected members (10, 11) carrying a locking device (17) and a first end a second axle (20, 21). The first axle (20) forms a bearing axle for the locking device and the second axle (21) cooperates with the locking device for activation thereof. The second axle (21) is located at a distance behind the first axle (20) and is arranged to act upon the locking device in such a way that when the line of action (26) from a load on the knee prosthesis passes through the second axle (21) or between the first (20) and the second axle, said second axle will act upon the locking device to activate it, while when said line of action (26) passes through the first axle or in front of it the second axle (21) will be unloaded and the locking device (17) inactivated.

11 Claims, 21 Drawing Sheets

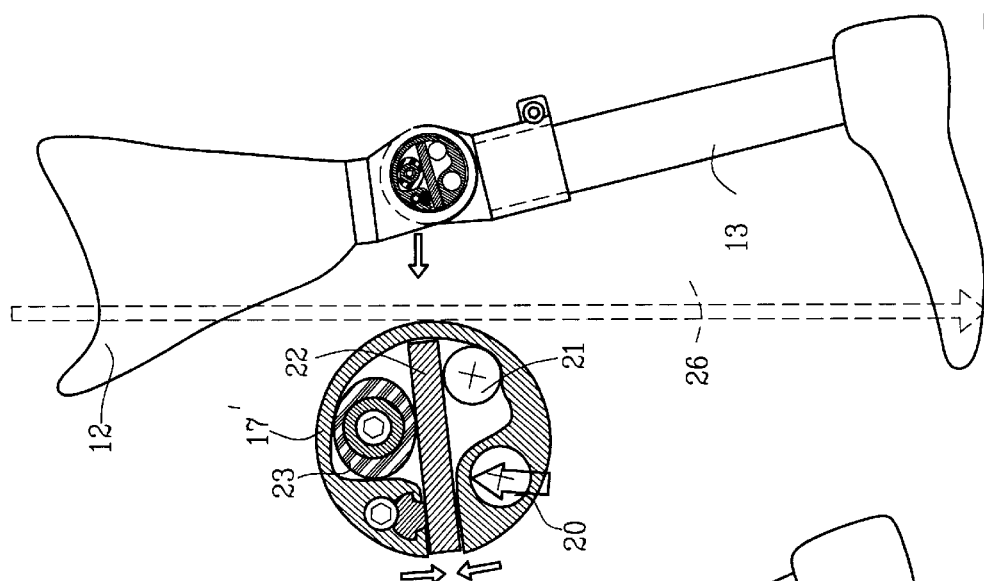
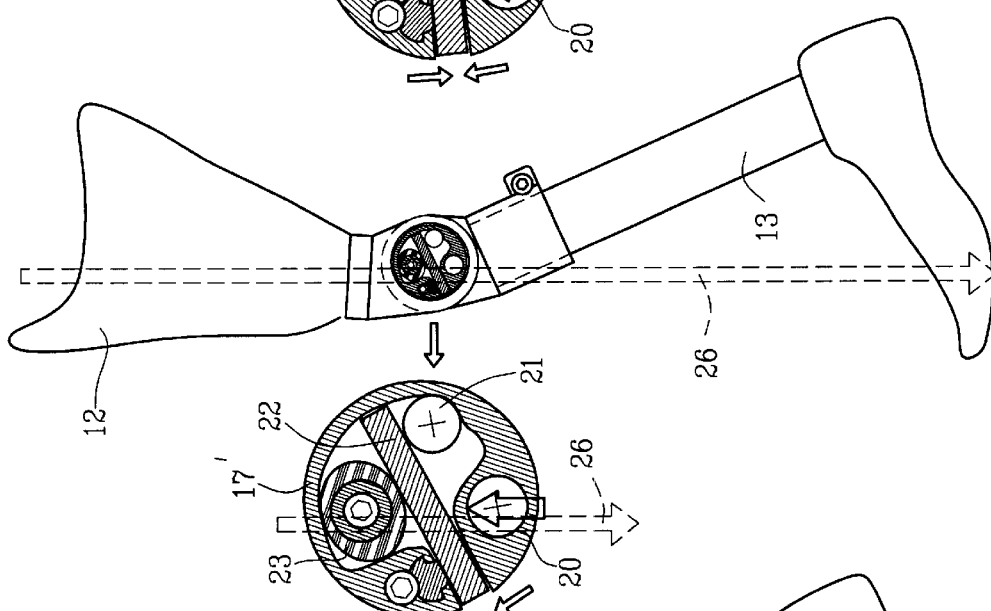
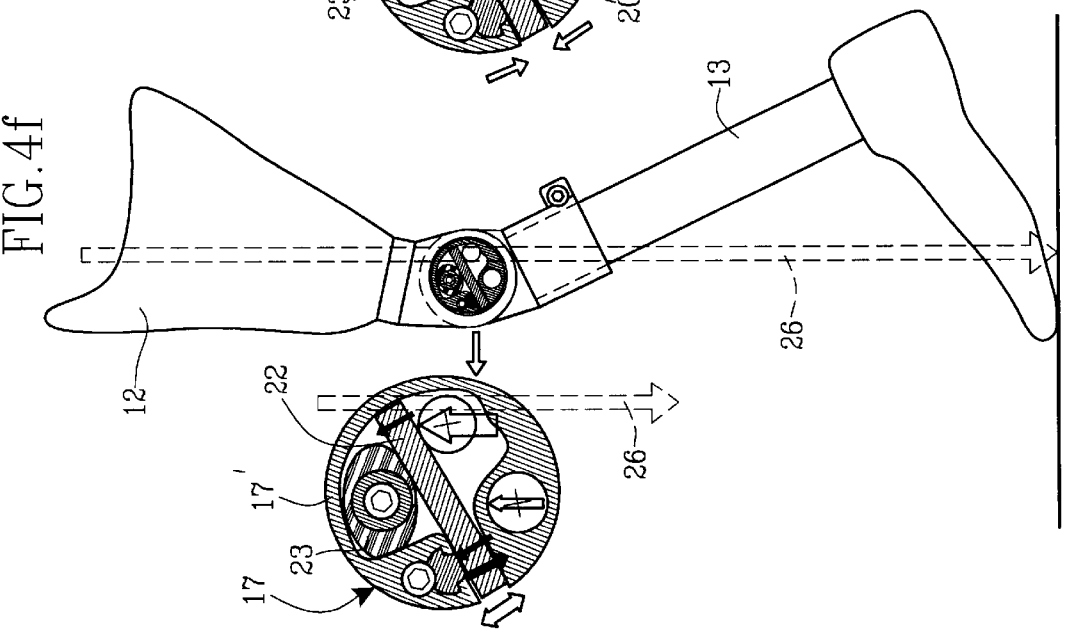

KNEE PROSTHESIS

This is a continuation-in-part of U.S. patent application Ser. No. 09/250,577 filed on Feb. 16, 1999 now U.S Pat. No. 6,159,248 which claims benefit of Prov. Appl. No. 60/083,318 filed Apr. 28, 1998.

TECHNICAL FIELD

The present invention refers to a knee prosthesis comprising two pivotally interconnected members carrying a locking device and a first and a second axle, said first axle forming a bearing axle for the locking device and the second axle cooperates with the locking device for activation thereof said locking device is arranged to permit said members to pivot in an unloaded position but prevent pivoting from extended to bent position when loaded.

BACKGROUND OF THE INVENTION

Traditional friction locks in knee prostheses will lock when there is a load acting on them, i.e. when some part of the body weight rests on the artificial knee. This takes place in a still standing position as well during the walking phase at heel strike when the heel hits the ground, and during toe off supporting oneself on the toe while extending the leg to initiate the swing phase when the leg swings freely in the air.

At normal walking without a prosthesis one starts already during toe off to flex the knee-joint to initiate the swing phase fore all body weight is has been removed from the leg in question. This is not possible with knee prostheses with a friction lock of the conventional kind. This involves an unnatural walking and makes walking in stairs and broken ground and cycling difficult since the knee prosthesis will lock as soon as it is loaded.

Knee prostheses with friction locks in the form of a brake drum are disclosed in U.S. Pat. Nos. 4,206,519 and 4,351,070. In the last mentioned document there is a linkage transferring motions in the hip axis to the locking device in order to control the locking function thereof in response to the torque of the hip axis. PCT Publication WO 97/10781 discloses a knee prosthesis with a friction lock in the form of a resiliently deformable substantially C-shaped member cooperating with an axle. The C-shaped member can be rotated about the axle in unloaded position, but in a locked position be deformed and locked to the axle.

SUMMARY OF THE INVENTION

The present invention provides a knee prosthesis, which permits rotation of the knee-joint in an unloaded position and when it still is under a body load during toe off when supporting oneself on the toe while extending the leg to initiate the swing phase, but which locks against rotation from extended to flexed position at other loaded positions, for example during heel strike when supporting oneself on the heel and during mid stance when supporting oneself on the whole foot. The present invention also provides a geometric sensitivity of the locking device, due to the fact that the bearing axle of the locking device, said first axle, is arranged out of center of the locking device, so that depending on where a load line from a load on the knee-joint passes through it with respect to its geometrical center and with respect to said first axle, the rotating part of the locking device will either be in balance, at which it is unactivated, or out of balance, at which it will be activated.

A further important advantage of the invention is that the knee-joint has a freewheel effect in such a way that it can always rotate from flexed to extended position also under load. By this, for example walking on stairs will be possible. The knee-joint will however lock immediately again if it is rotated in the opposite direction, for example from extended to flexed position, under such load that the locking device is activated.

DESCRIPTION OF DRAWINGS

FIGS. 4a–f illustrates the function of the knee prosthesis during the different phases of the walking cycle.

DESCRIPTION OF EMBODIMENTS

Figure 1:
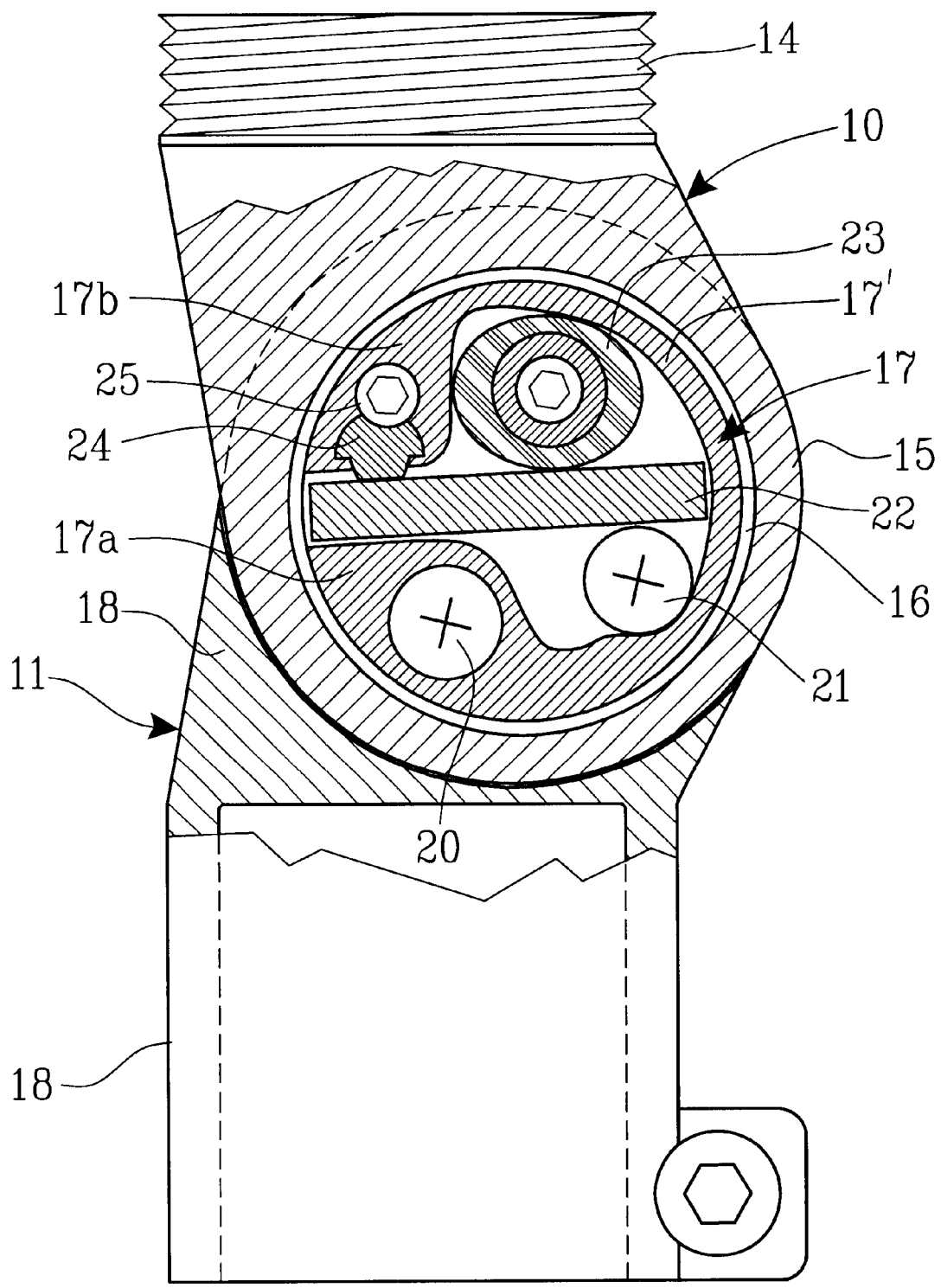
FIG. 1 is a longitudinal section through n embodiment of a knee prosthesis according to the invention in unloaded position.
Figure 2:
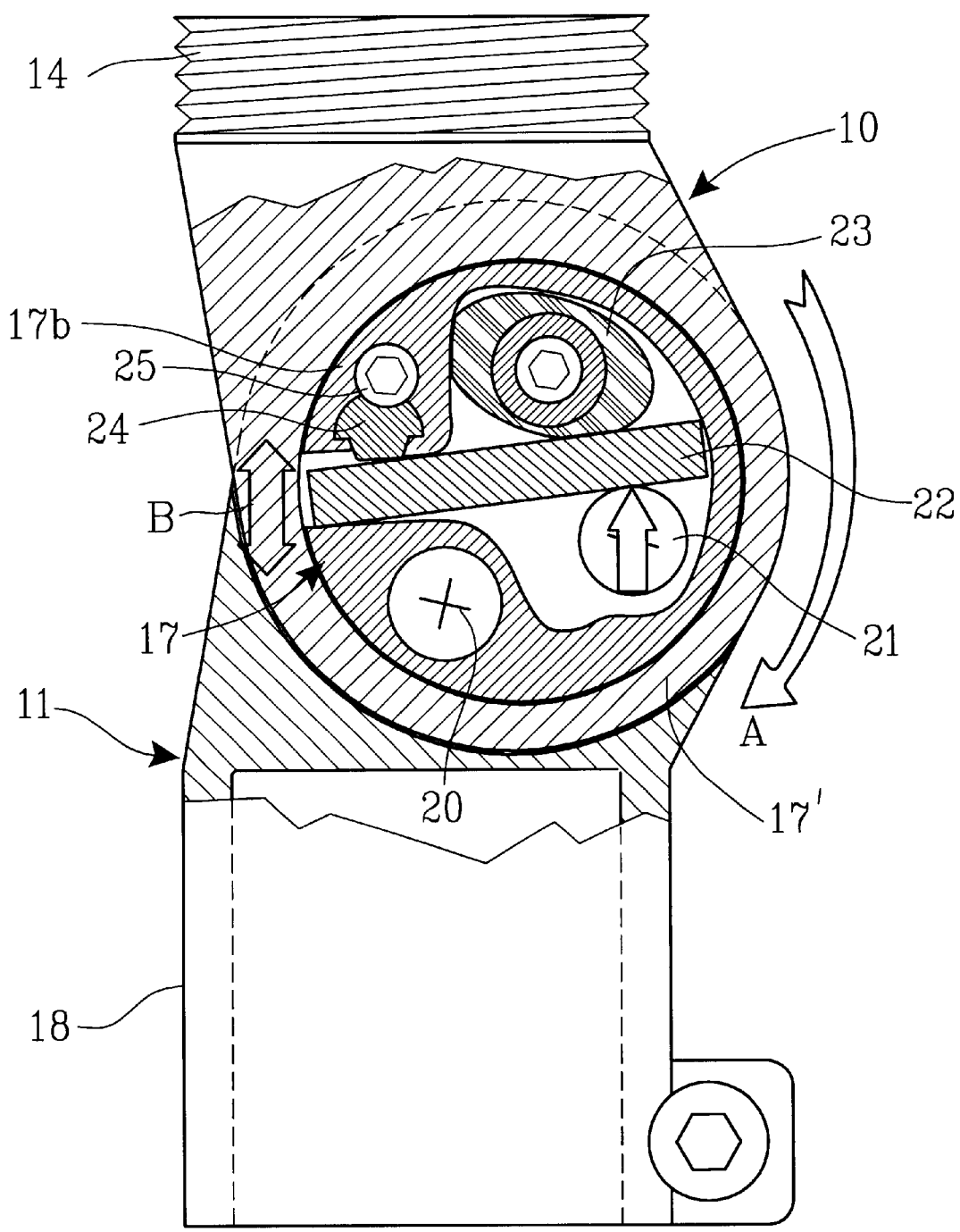
FIG. 2 shows the knee prosthesis according to FIG. 1 in loaded position.
Figure 3:
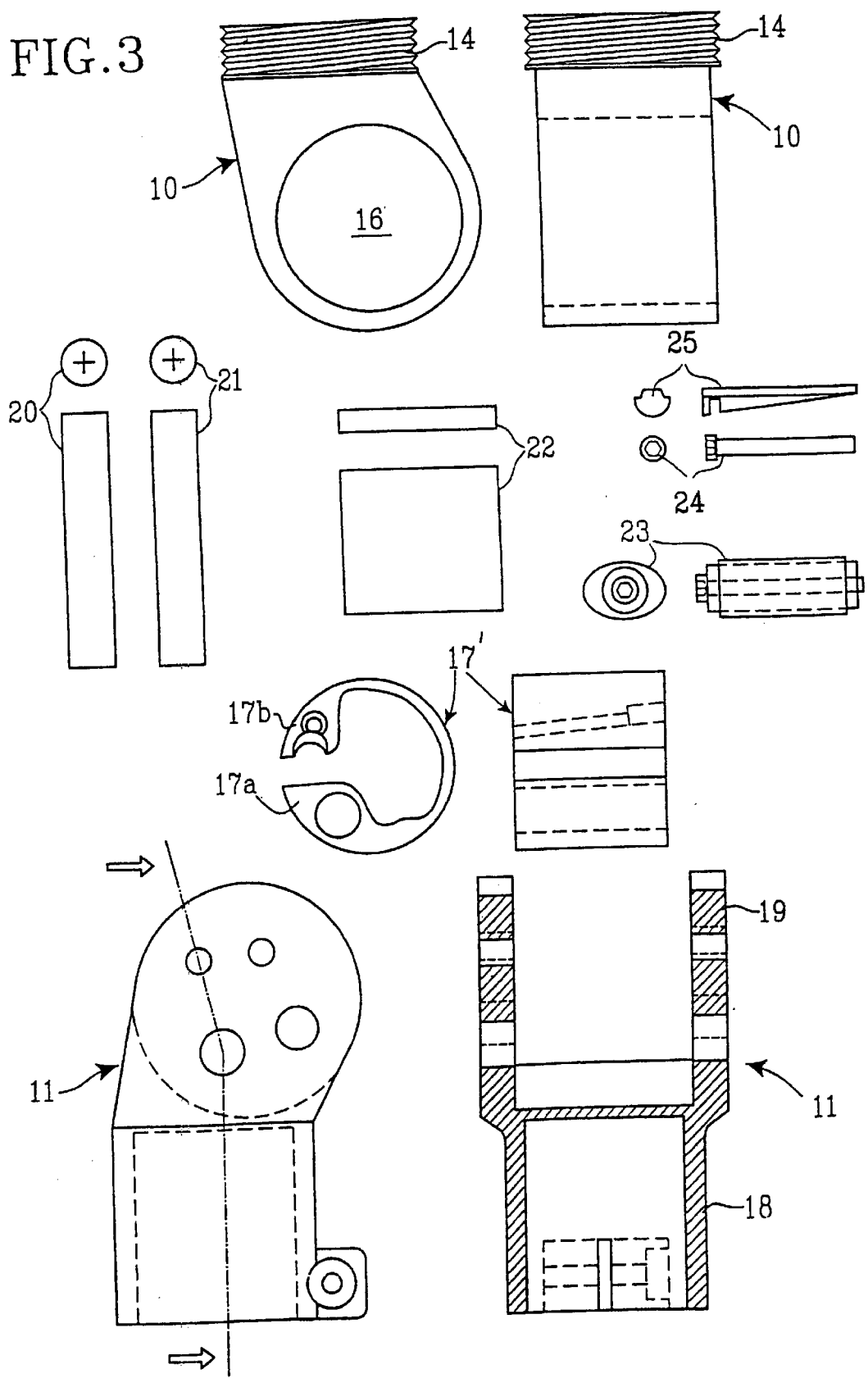
FIG. 3 is an exploded view of the knee prosthesis according to FIGS. 1 and 2.

The knee prosthesis according to the embodiment shown in FIGS. 1–4 comprises an upper and a lower member 10 and 11, which are pivotally interconnected. The upper member is intended to be attached to a prosthesis sleeve 12 and the lower member to a lower leg prosthesis 13 (FIG. 4) having a foot prosthesis 13a connected thereto.

The upper knee prosthesis member 10 comprises a socket, in the shown embodiment a threaded socket 14, for connection to a prosthesis sleeve, and a housing portion 15 with a through opening 16 for receiving a locking device 17 in the form of a brake shoe 17'. The lower knee prosthesis member 11 is provided with a sleeve-shaped socket 18 for connection to a lower leg prosthesis 13, and a yoke-shaped upper portion 19 between the shanks 19a and b of which-the housing portion 15 of the upper knee prosthesis member 10 is received.

One shank 17a of the brake shoe 17' holds a bearing for the first axle 20 while the second shank 17b supports friction adjustment means 24 and 35 for controlling the friction level during the different phases of the ealking cycle. These friction adjustment means comprises a conical wedge 25 and a screw 24 cooperating therewith. By tightening the screw 24 the wdge 25 is moved and can expand the brake shoe 17'. A friction adjustment could alternatively be done by squeezing together the shanks 19a and b of the yoke=shaped part 19. A brake lining, for example a plastic band, could be arranged on the outside of the rake shoe.

In the braking mechanism there is included besides the brake shoe 17' an activating member 22 in the form of a lever arm extending through the brake shoe 17' substantially across the axles 20 and 21. The brake shoe 17' has the shape of an open ring and the lever arm 22 extends in between the shanks 17a and b of the brake shoe. The lever arm 22 supports against the second axle 21 and can thereby be pressed upwards and in such a way force the shanks 17a and b to spring apart, at which the brake shoe 17' expands and is friction locked against the inside of the opening 16 forming a brake drum. Between the lever arm 22 and the brake shoe 17' on the opposite side of the lever arm with respect to the second axle 21 there is arranged an adjustable resilient element 23 against which the lever arm presses when it is activated by the second axle 21, said resilient element 23 thus limiting the action of the lever arm 22. The resilient element 23, which comprises a sleeve through which a screw 23a extends, can be made stiffer in order to adapt to the body weight of the wearer of the prosthesis and thus prevent that the knee-joint will lock too easily. The stiffness of the element 23 can be adjusted either by tightening the screw 23a, at which the sleeve is compressed, or by replacing the element 23 for stiffer or softer rubber element 23.

The lever arm 22 can optionally be made resilient to some extent, for example, by using a number of spring steel elements placed on top of each other, at which it will be possible to accomplish the light resilient knee flexion one normally makes when putting the heel in the ground, so called stans flex. The element 23 must in this case be relatively soft.

One shank 17a of the brake shoe 17' holds a bearing for the first axle 20 while the second shank 17b supports friction adjustment means 24.25 for controlling the friction level during the different phases of the walking cycle. These friction adjustment means comprises a conical wedge 25 and a screw 24 cooperating therewith. By tightening the screw 24 the wedge 25 is moved and can expand the brake shoe 17'. A friction adjustment could alternatively be done by squeezing together the shanks 19a and b of the yoke-shaped part 19. A brake lining, for example a plastic band, could be arranged on the outside of the brake shoe.

In FIG. 1 the knee-joint is shown in a position where the brake shoe 17' is unloaded and thus can be rotated within the opening 16 of the housing portion 15. If, however, a load (FIG. 2) is applied on the leg, the brake shoe 17' will be pressed downwards and at the same time rotate about the first axle 20 in the direction of the arrow A. When the brake shoe is rotated about the axle 20 the rear brake-activation axle 21 will meet the lever arm 22, which as described above forces the brake shoe 17' to expand (arrow B) and lock against the inside of the opening 16 in the housing portion 15. The knee joint is by this locked.

If the knee joint is rotated from a flexed to an extended position, for example, in the opposite direction with respect to the arrow A, during loading, the friction between the inside of the opening 16 in the housing portion 15 and the brake shoe 17' will force this to rotate back to the position for unloaded position (dashed lines). The lever arm 22 will then leave the axle 21 and the knee joint can be rotated freely in the counter clockwise direction. It will however immediately lock again if, during loading, it is rotated in the clockwise direction.

Figure 4A:
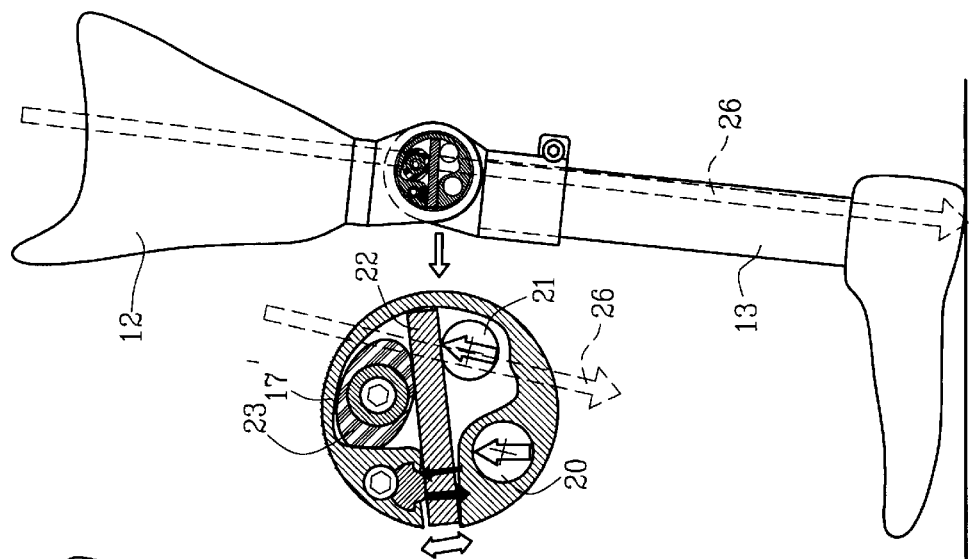

In FIGS. 4a–f the braking function of the knee prosthesis is shown during the different phases of the walking cycle. In FIG. 4a the heel strike position is shown, in which the heel strikes the ground and the wearer starts to put a load on the leg in question. The body weight line illustrated by the arrow 26 in this position passes right through the second axle 21 or behind this, which means that the whole body weight will force the brake shoe 17' to rotate downwards about the axle 20. The lever arm 22 will then meet the axle 21, which in turn presses against the lever arm 22 which forces the brake shoe 17' to expand and lock the knee joint prosthesis. If the bending force would increase, the knee joint will use the front axle 20 as a fixed point and the distance between the axles 20 and 21 will act as a lever arm and increase the braking force proportionally to the increasing bending force. This will keep the knee locked independently of the bending forces, which act upon the knee joint.

Figure 4B:
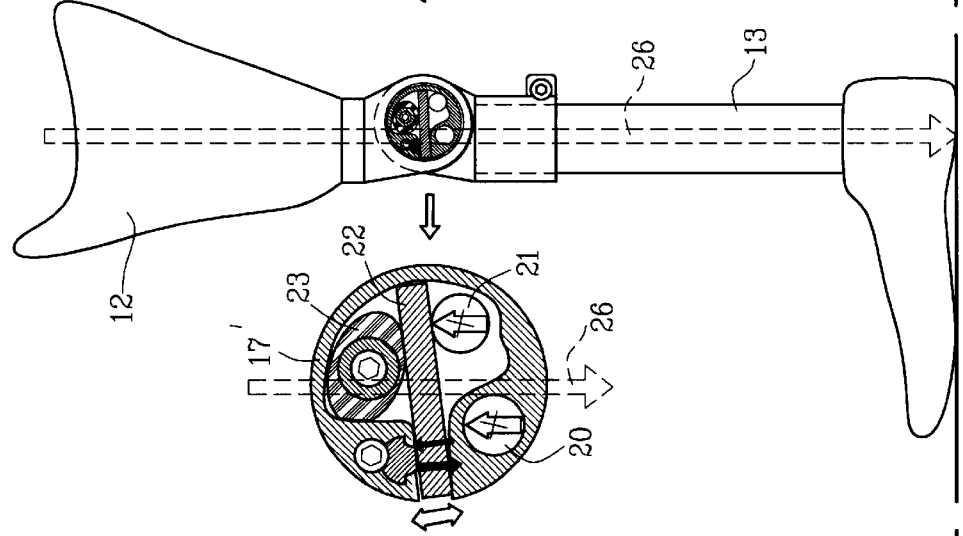

In FIG. 4b is shown the mid stance position when the whole foot rests against the ground and the body weight acts essentially right through the leg in parallel therewith. The body weight line 26 passes in this position between the two axles 20 and 21, which means that both the front 20 and the rear axle 21 are loaded, at which the latter still presses against the lever arm 22 and locks the brake shoe 17'. If the prosthesis wearer in this position would try to flex the knee joint this would only lead to an increased force on the rear brake-activating axle 21 in the way described above.

Figure 4C:
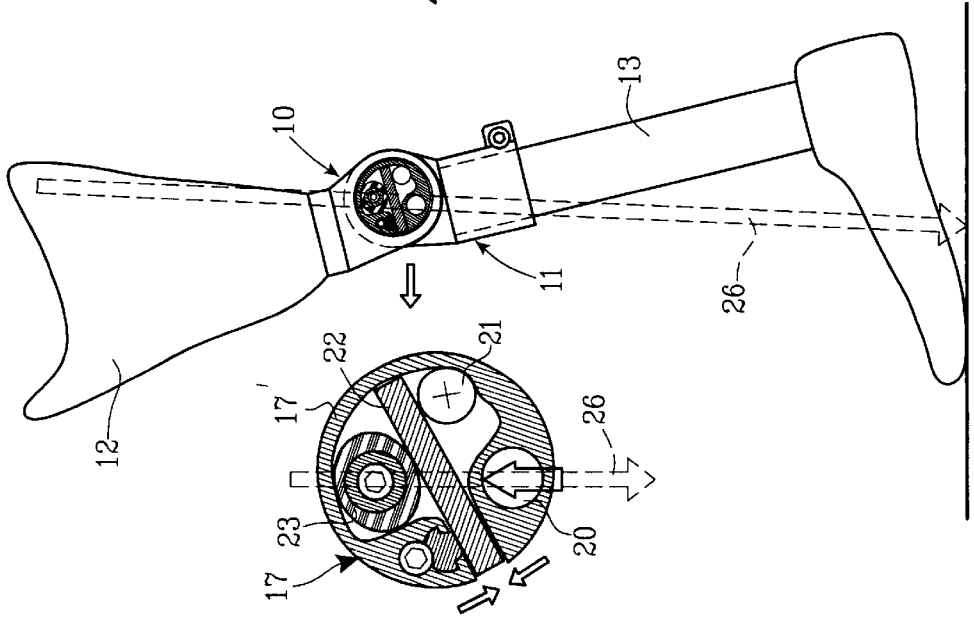

In FIG. 4c is shown the toe off phase when supporting oneself on the toe while extending the leg to initiate the swing phase with the leg swinging freely in the air. A part of the body weight rests in this position still upon the leg. At normal walking, a flexing of the knee joint is already initiated in this position, in order to initiate the swing phase before all body weight has been removed from the leg in question. The body weight line 26 passes in this position from the toe part of the foot prosthesis 13a through or in front of the front axle 20, the bearing axle, at which the body weight rests on the front axle 20. No load acts on the rear brake-activation axle 21, at which the knee joint is free to rotate for initiating the swing phase of the walking cycle.

In FIGS. 4d–f are shown different stages of the initiation of the swing phase of the walking cycle with the knee joint prosthesis in different positions. In FIG. 4d is shown an extended leg in toe off position at which the body weight line 26 passes from the toe portion of the foot prosthesis 13a and in front of the front axle 20. In a corresponding way as described in connection with FIG. 4c the brake function is inactivated despite that body weight is still loading the leg and the knee joint can be flexed for initiating the swing phase.

FIG. 4e shows the toe off position with the knee flexed approximately 45°. Most of the body weight has now been removed from the leg, but there can still be enough load for activating the brake function. However the body weight line 26 will still be in front of the front axle 20, and no load will act upon the rear brake-activation axle 21. If however the prosthesis wearer in this position would stumble the body weight can be moved backwards by extending the thighbone and by that have the brake activated.

In FIG. 4f is shown the end of the toe off phase just as the leg has been unloaded from the body weight. The leg is now flexed approximately 55° and the body weight line 26 passes through the rear brake-activating 21, but since the leg is unloaded the knee joint can be rotated. If however the prosthesis wearer in this position would stumble or something else unexpected would happen the prosthesis wearer can activate the brake by extending the thighbone.

Figure 5A:
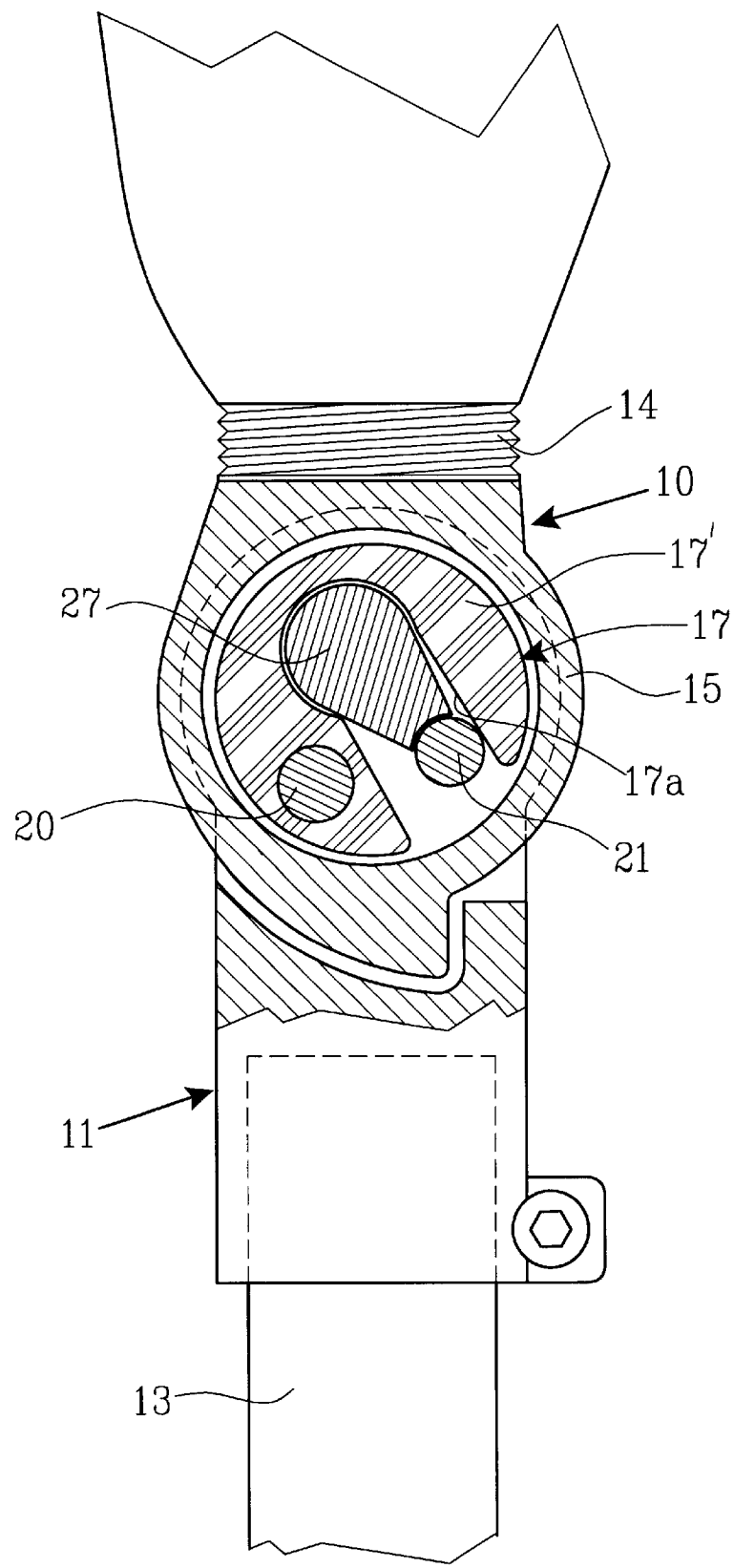
FIGS. 5a and b show longitudinal sections through a second embodiment of the knee prosthesis in unloaded and loaded positions respectively.
Figure 5B:
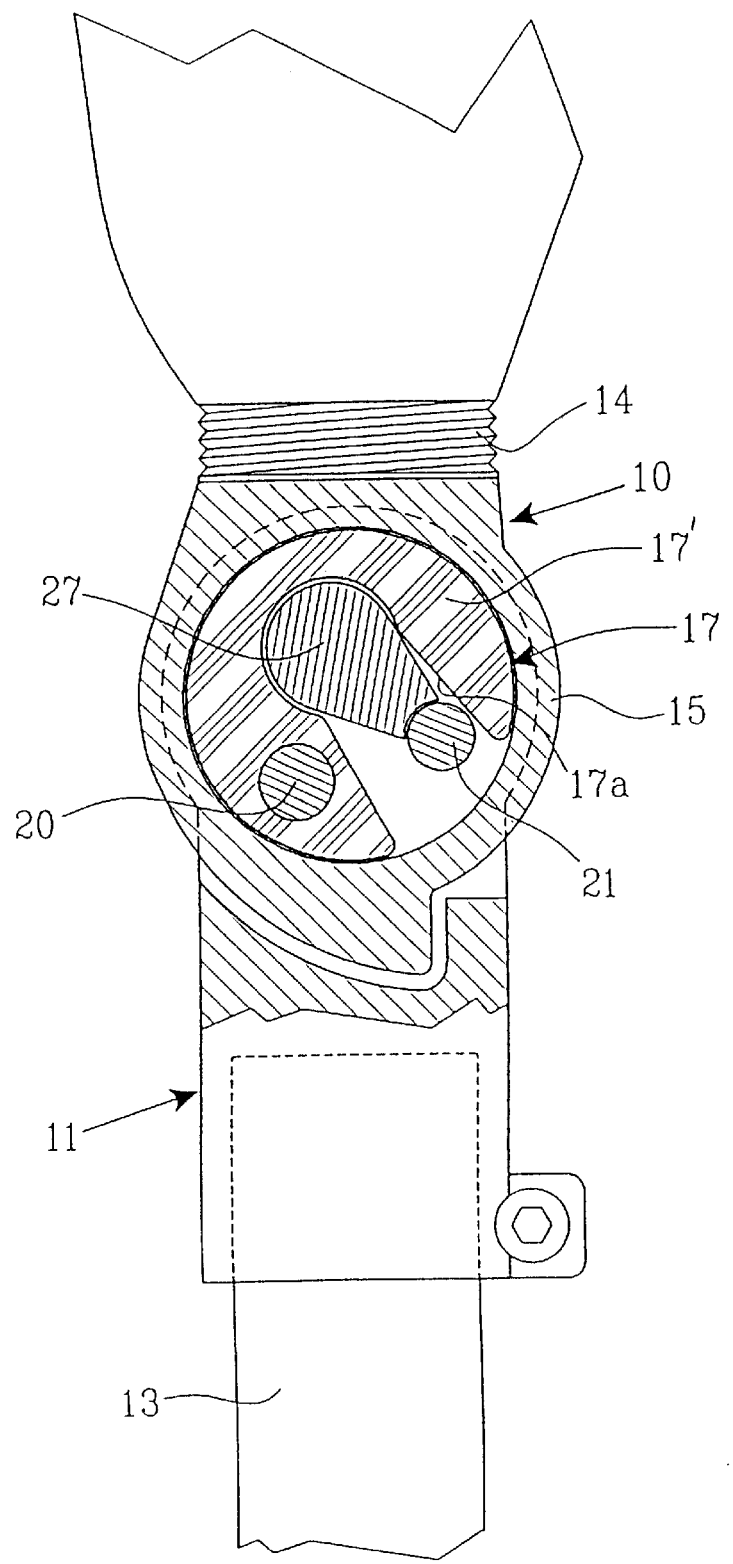

The embodiment shown in FIGS. 5a and b differs from the one described above by the fact that the brake-activating axle 21 acts directly upon an inclined end surface 27 on the shank 17b of the brake shoe 17'. This embodiment functions in a corresponding way as the previous one since the brake shoe 17' in unloaded position (FIG. 5a) can be rotated in the opening of the housing portion 15. In such loaded positions (FIG. 5b) when the body weight line passes between the axles 20 and 21 right through the second axle 21 or behind it, the body weight will force the brake shoe 17' to rotate downwards about the axle 20. The inclined surface 27 on the brake shoe will then meet the axle 21, which forces the brake shoe 17' to expand and lock against the inside of the housing portion 15, at which the knee is locked. In the positions when the body weight line passes through or in front of the front axle 21, the bearing axle, and no load acts upon the rear brake-activating 21, the knee joint will be free to flex.

Figure 6A:
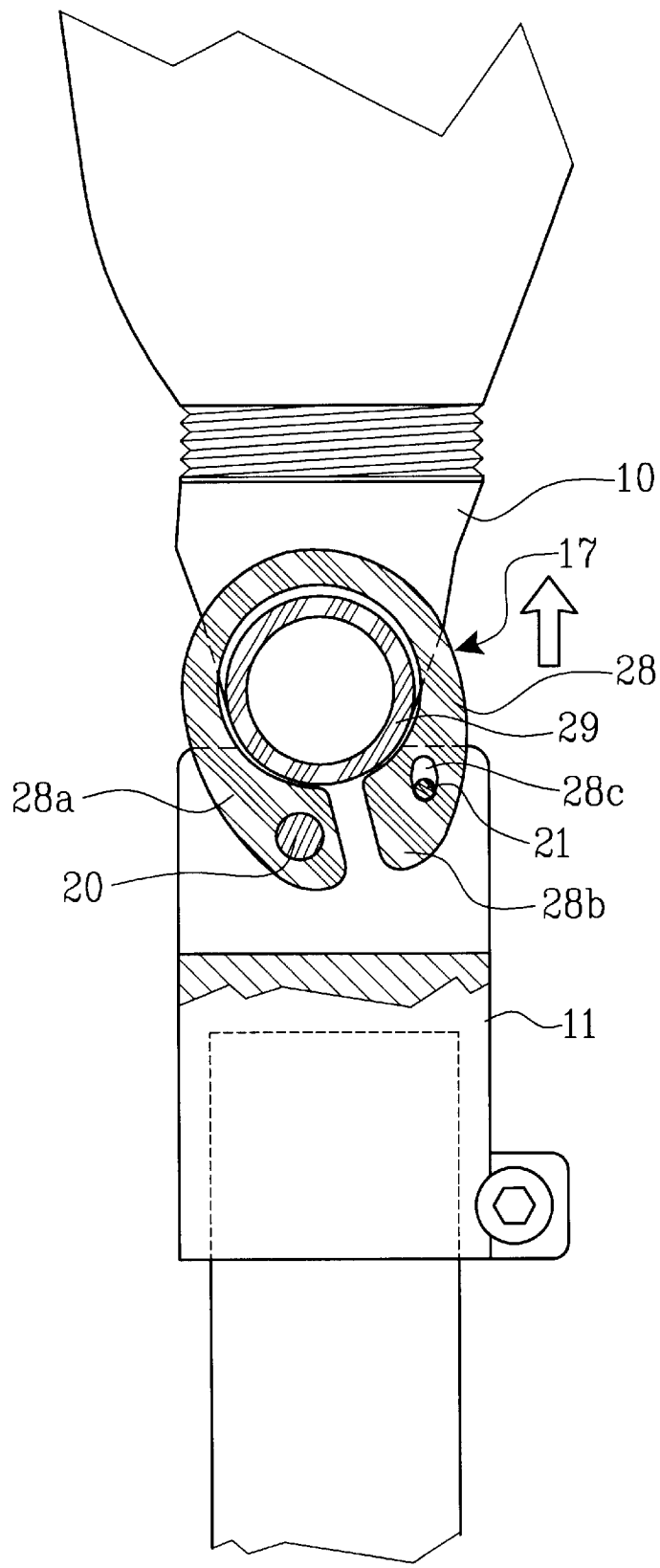
FIGS. 6a and b show longitudinal sections through a third embodiment of the knee prosthesis in unloaded and loaded positions respectively.

In FIGS. 6a and b it is shown an embodiment where the knee joint has a friction lock in the form of a substantially C-shaped resilient member 28 arranged about a tube-shaped axle 29 connected to the upper prosthesis member 10. The first axle 20 extends through one shank 28a of the C-shaped member 28 and the second brake-activating axle 21 extends through the second shank 28b of the C-shaped member 28 through a groove 28c arranged therein.

Figure 6B:
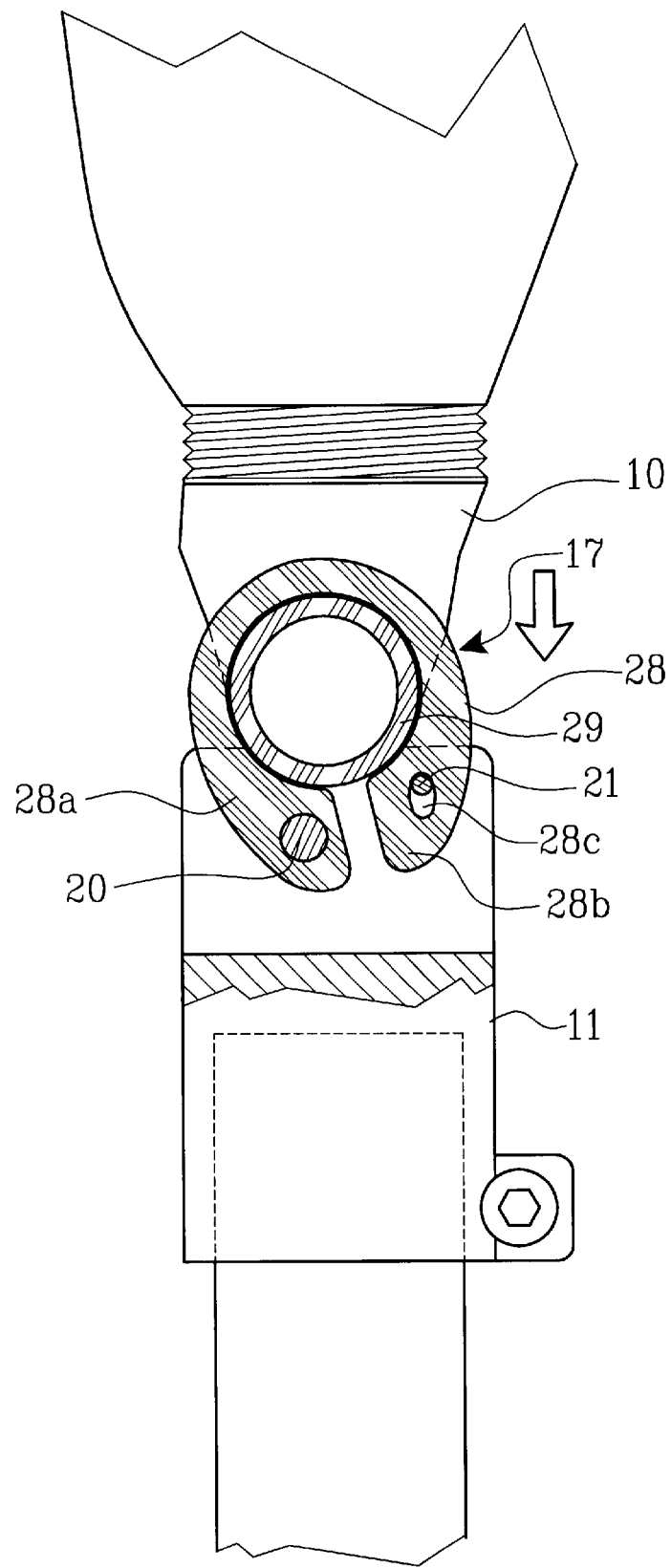

In an unloaded position (FIG. 6a) and in a position where the line of action from a loading on the knee prosthesis passes through the first axle 20 or in front thereof the C-shaped member 28 will be unloaded and rotatable about the axle 20 and slidable on the inner tube-shaped axle 29. If however the knee joint is loaded (FIG. 6b) in such a way that the line of action passes through the second brake-activating axle 21 or between the first and the second axle 20, 21, the body weight will force the member 28 to rotate downwards about the axle 20. The shank 28b of the C-shaped member 28 can only be moved in the direction permitted by the groove 28c, which extends in such a direction that the shank 28a when the knee joint is loaded will clamp about the inner tube-shaped axle 29, at which the knee joint is locked.

Figure 7A:
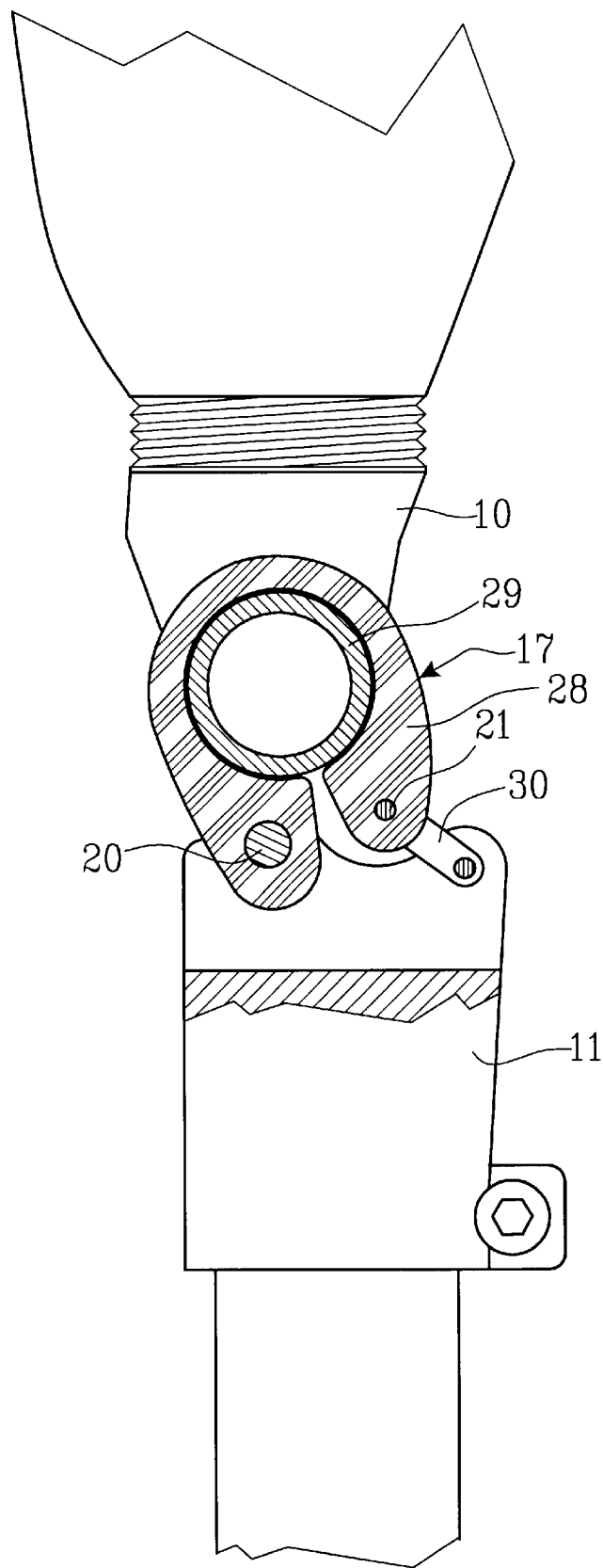
FIGS. 7a and b show longitudinal sections through a fourth embodiment of the knee prosthesis in unloaded and loaded positions respectively.
Figure 7B:
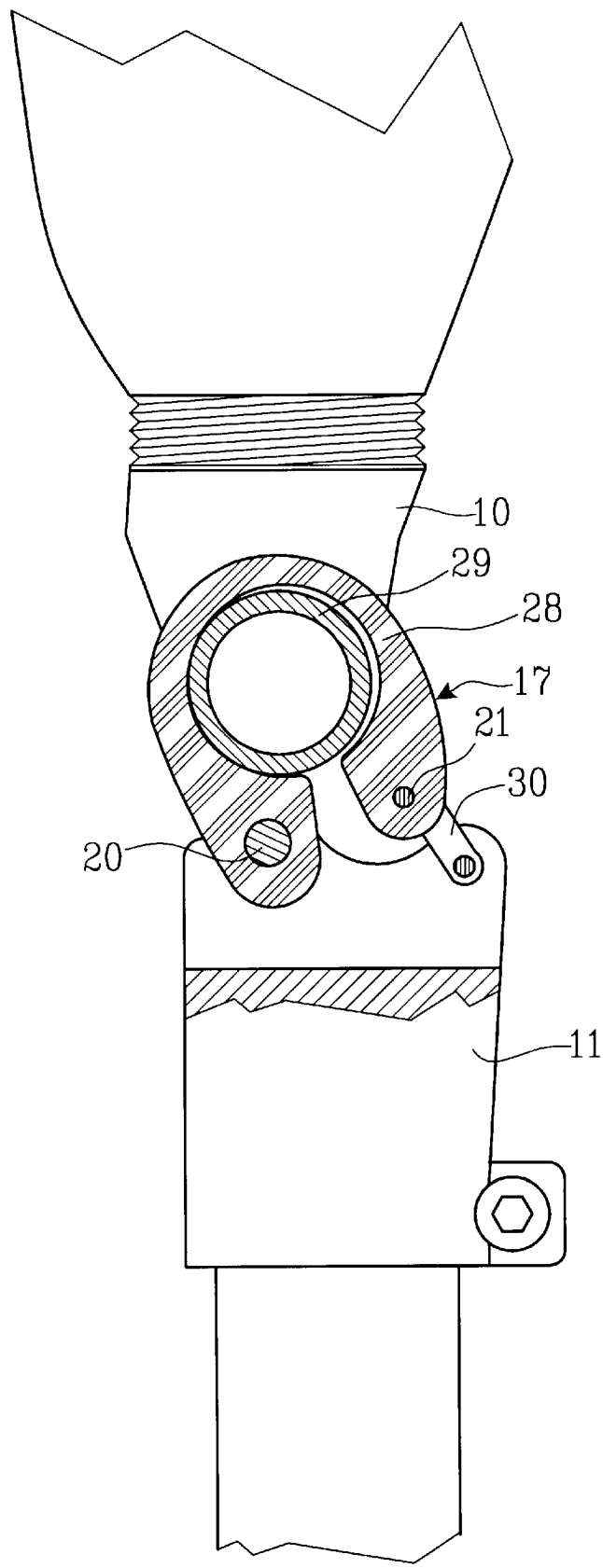

In FIG. 7 it is shown a further embodiment, which differs from the one shown in FIG. 6 by the fact that the brake-activating axle 21 is connected with the lower prosthesis member 11 by means of a link 30. In FIG. 7b the knee joint is shown in an unloaded position at which the C-shaped member 28 is free to rotate about the axle 21 and slide on the inner tube-shaped axle 29. If however the knee joint is loaded in such a way that the line of action passes through the second brake-activating axle 21 or between the first and the second axle 20, 21 the body weight will force the member 28 to rotate downwards about the axle 20. The link 30 will then force the shank 28a to clamp about the inner tube-shaped axle 29, at which the knee joint is locked, as is shown in FIG. 7a.

Figure 9:
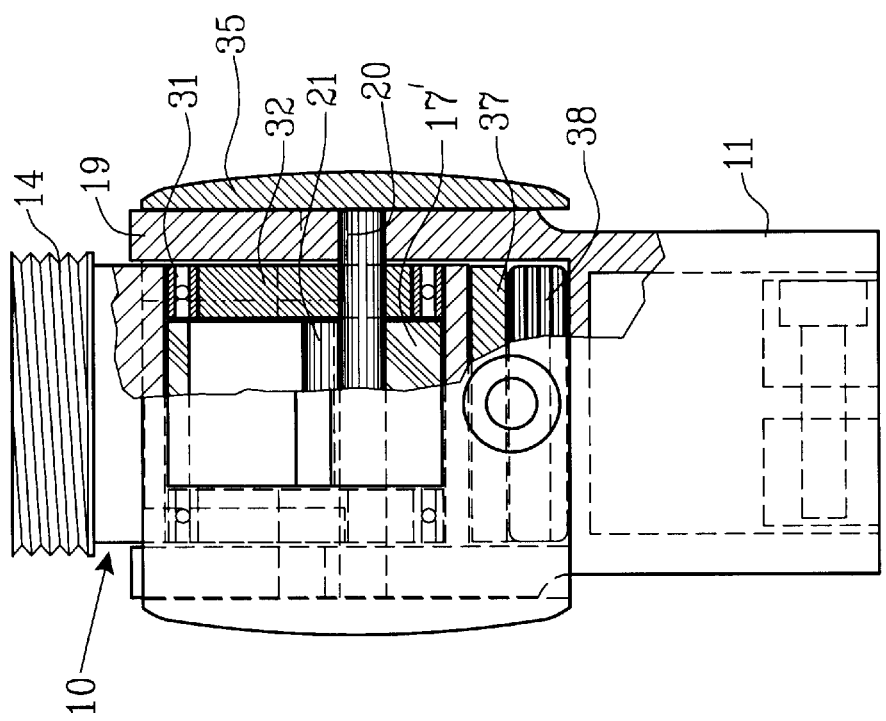
FIG. 9 is a front view of the knee prosthesis according to FIG. 8.
Figure 8:
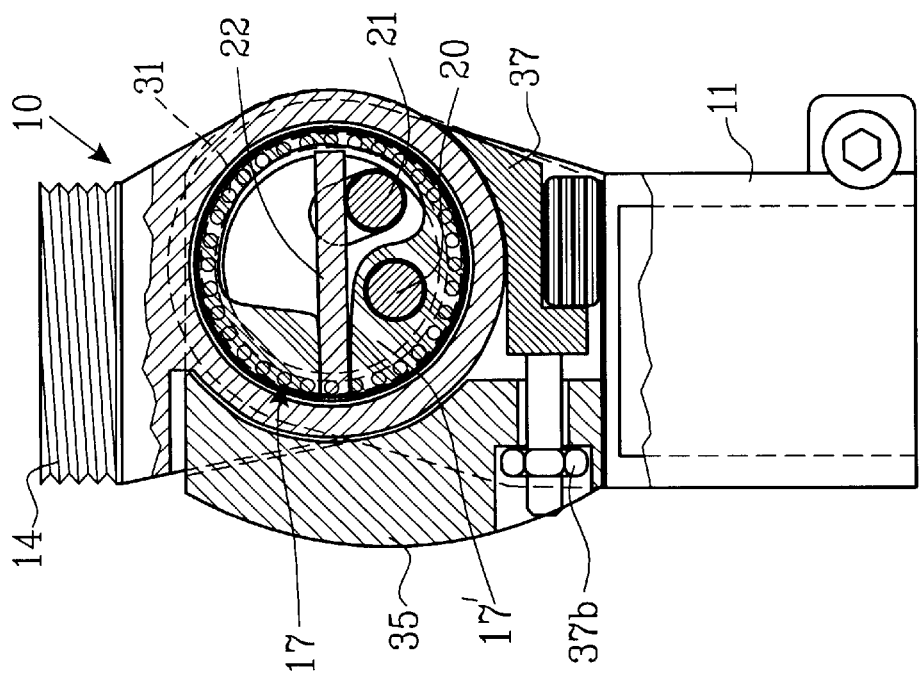
FIG. 8 shows a longitudinal section through a fifth embodiment of the knee prosthesis in unloaded position.
Figure 10:
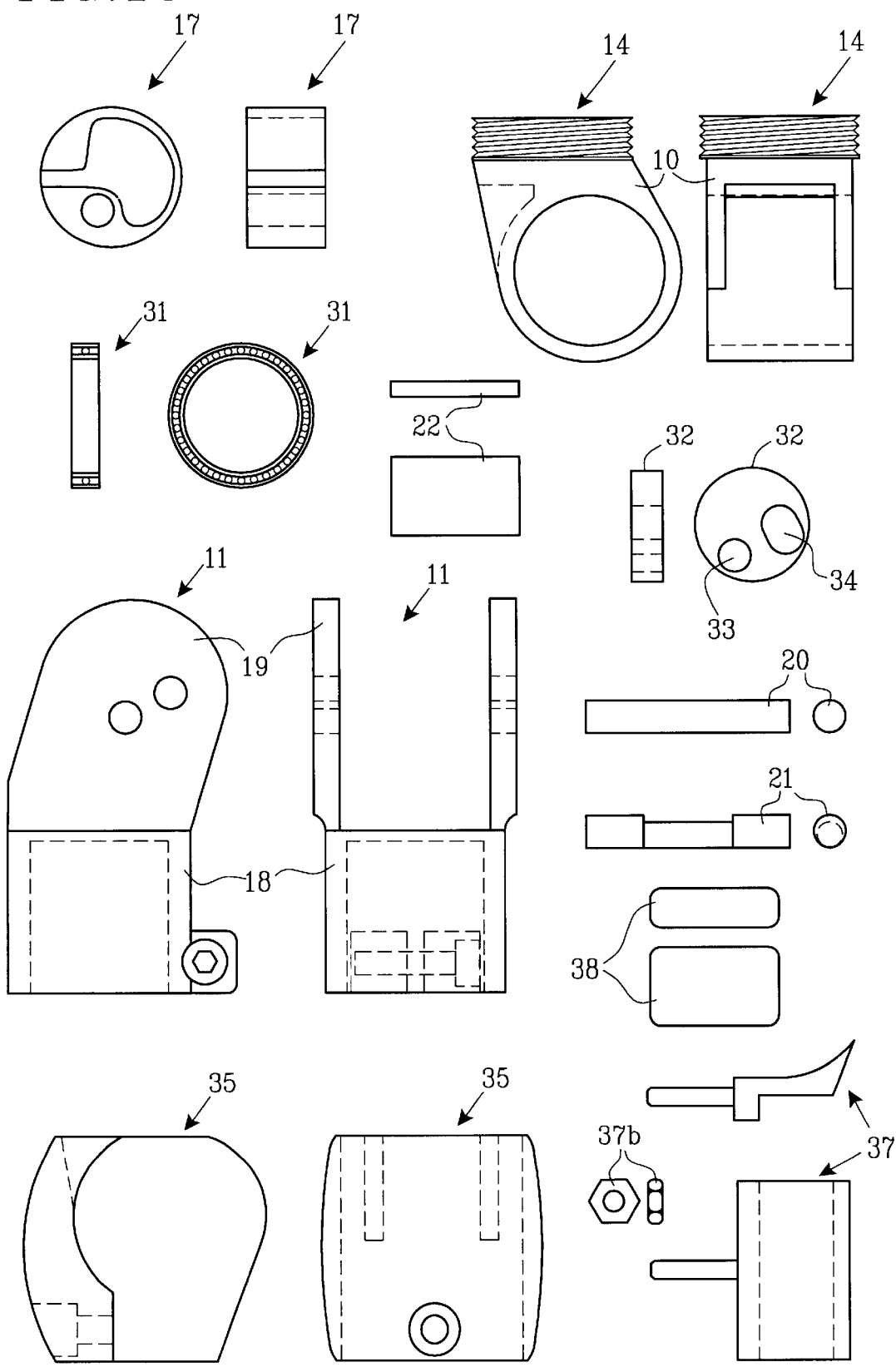
FIG. 10 is an exploded view of the knee prosthesis according to FIGS. 8 and 9.

The embodiment according to FIGS. 8–10 is similar to the one shown in FIGS. 1–4 and differs mainly therefrom by the fact that the brake shoe 17' has been made shorter in order to make space for a ball bearing 31 on both sides. By this, the lateral stability of the knee joint is improved. The stabilization of the ball bearings 31 is transferred via a plate 32 placed in the centre of the bearings, said plate having a hole 33 for the front axle 20 and an oblong hole 34 for permitting the brake-activating movement of the second axle 21. The resilient element 23 in the embodiment according to FIGS. 1–4 has been replaced by a functionally corresponding member 38. The friction adjusting means 24–25 according to FIG. 14 has been replaced by the parts 35, 37 and 39.

The upper knee joint member 10 has a lower part-cylindrical outer surface 10a. The housing member 35 is attached to the lower knee joint member 11 by means of the adjusting means 37 and the nut 37b. The resilient element 38 is placed under the adjusting means 37 and will assist this to press the upper knee joint member 10 and its part-cylindrical surface 10a against the housing portion 35 and its corresponding surface 35a. If the nut 37b is tightened, the adjusting means 37 will press harder against the resilient element 38 since this is forced to slide downwards along the part-cylindrical surface 10a. The upper knee joint member 10 will then be clamped between the adjusting means 37 and the housing portion 35 actuated by the compressed resilient element 38. This gives a frictional resistance as the knee joint member 10 is rotated. The inner brake shoe is now not needed for braking the swing movement of the leg but is only used for locking the knee joint. The resilient element 38 has also the same function as the element 23 in FIG. 3. In order to load the brake shoe 17' and the upper knee joint member 10 until a rotation is initiated about the first axle 20 and activate the brake, the resilient element 38 has to be compressed via the adjusting means 37 in the movement about the first axle 20.

Figure 11:
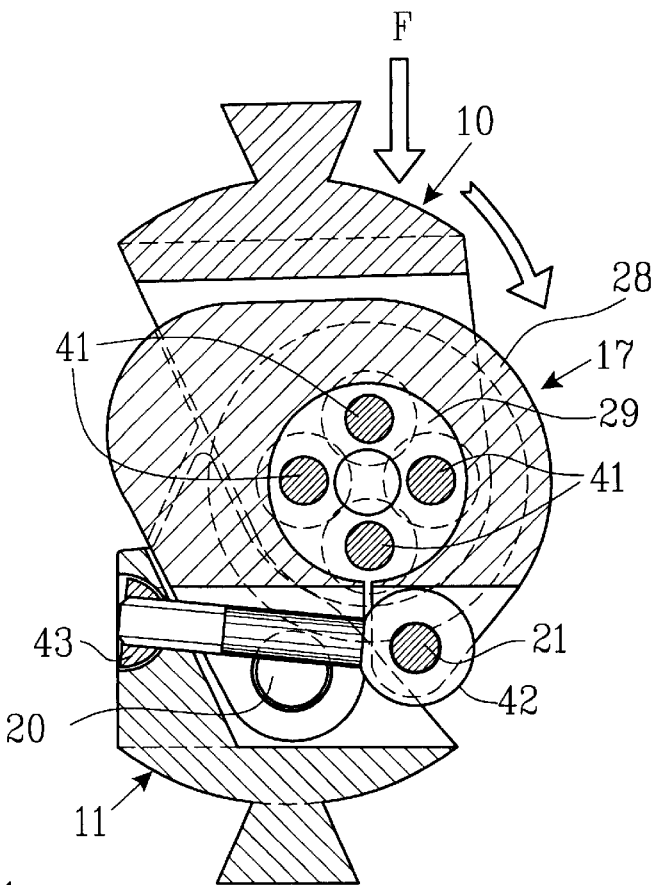
FIG. 11 is a longitudinal section through sixth embodiment of the knee prosthesis.
Figure 12:
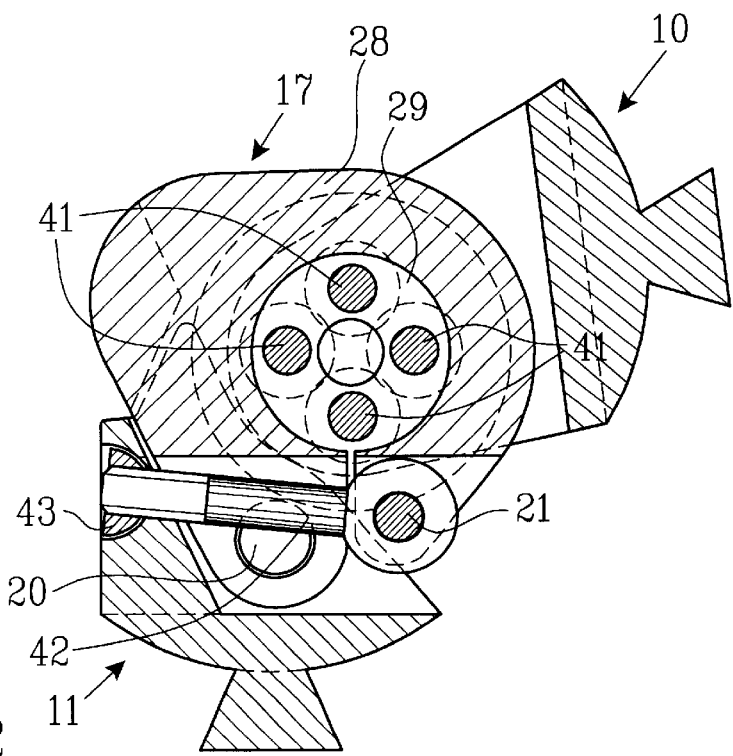
FIG. 12 is a corresponding section as FIG. 11 but showing the knee prosthesis in flexed position.
Figure 13:
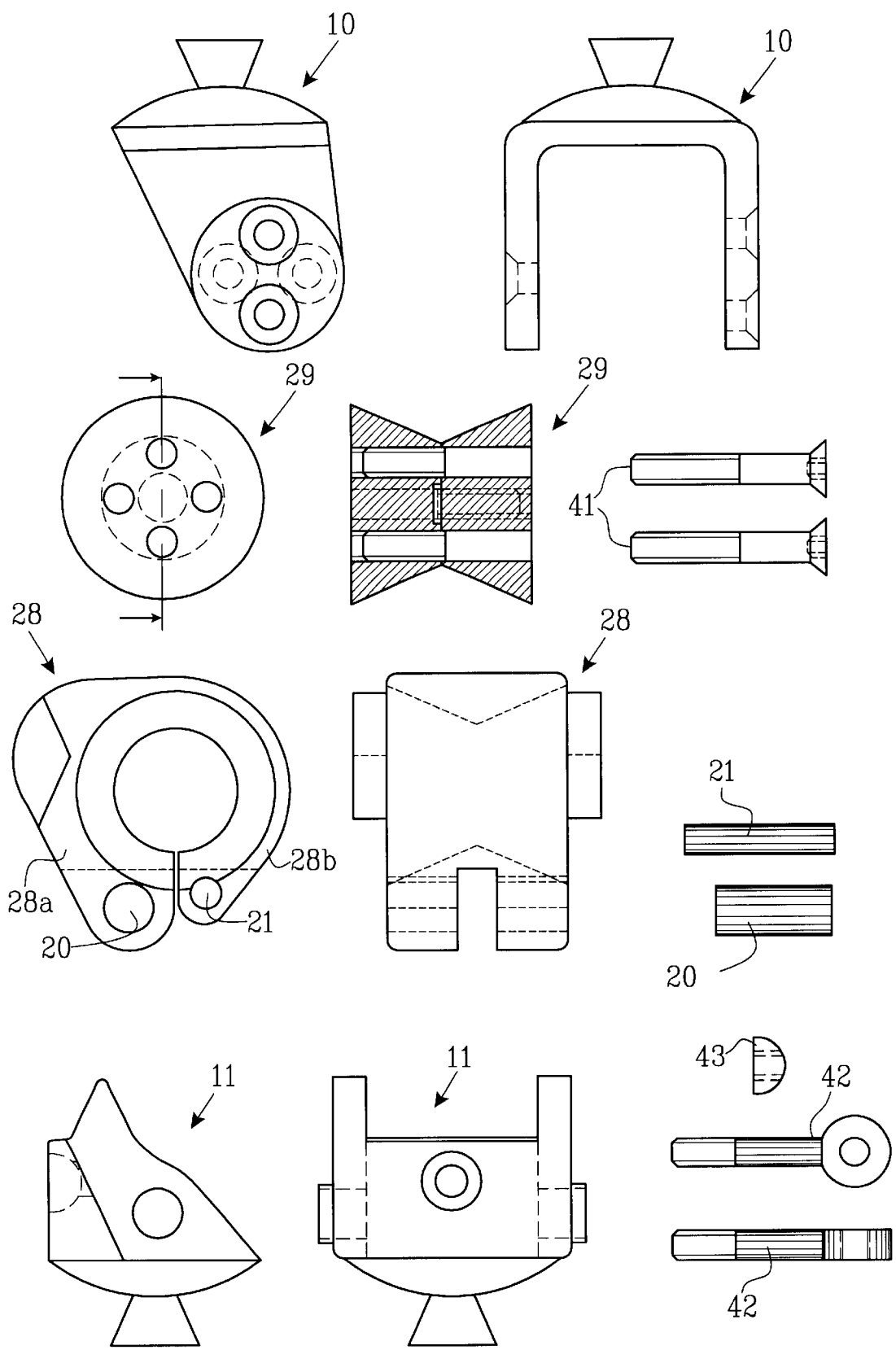
FIG. 13 is an exploded view of the knee prosthesis according to FIGS. 11 and 12.

The embodiment according to FIGS. 11–13 are similar to the ones shown in FIGS. 6–7 by the fact that it also comprises a friction lock in the form of a substantially C-shaped resilient member 39 arranged to clamp about an axle for locking the knee joint. This axle in this case comprises a drum having the shape of two truncated cones interconnected at their narrow end surfaces. The drum 29 thus has two conical surfaces that taper towards the mid portion of the drum. The drum 29 is by means of mounting bolts 41 attached to the upper prosthesis member 10. By the conical design of the drum/pivot axle 29 axial as well as well as radial forces can effectively be taken up effectively, at which a laterally very stable knee joint is provided.

The first axle 20 extends through one shank 28a of the C-shaped member 28 acting as a bearing housing and brake clip and the second 28b. The brake-activating axle 21 is connected to the lower prosthesis member by means of the link 42 and the fastening member 43. The link 42 corresponds to a link 30 in FIG. 7.

When a force F is loading the knee joint behind the front axle 20 (FIG. 11) the C-shaped member 28 acting as a bearing and brake lip is forced to rotate downwards about the axle 20 in the direction of the arrow. The shank 28b will then pull the axle 20, which by its anchorage in the member 28 forces the same, while having the brake-activating axle 21 as a holder-on, to clamp about the drum 29 and by that lock the knee joint.

Figure 14:
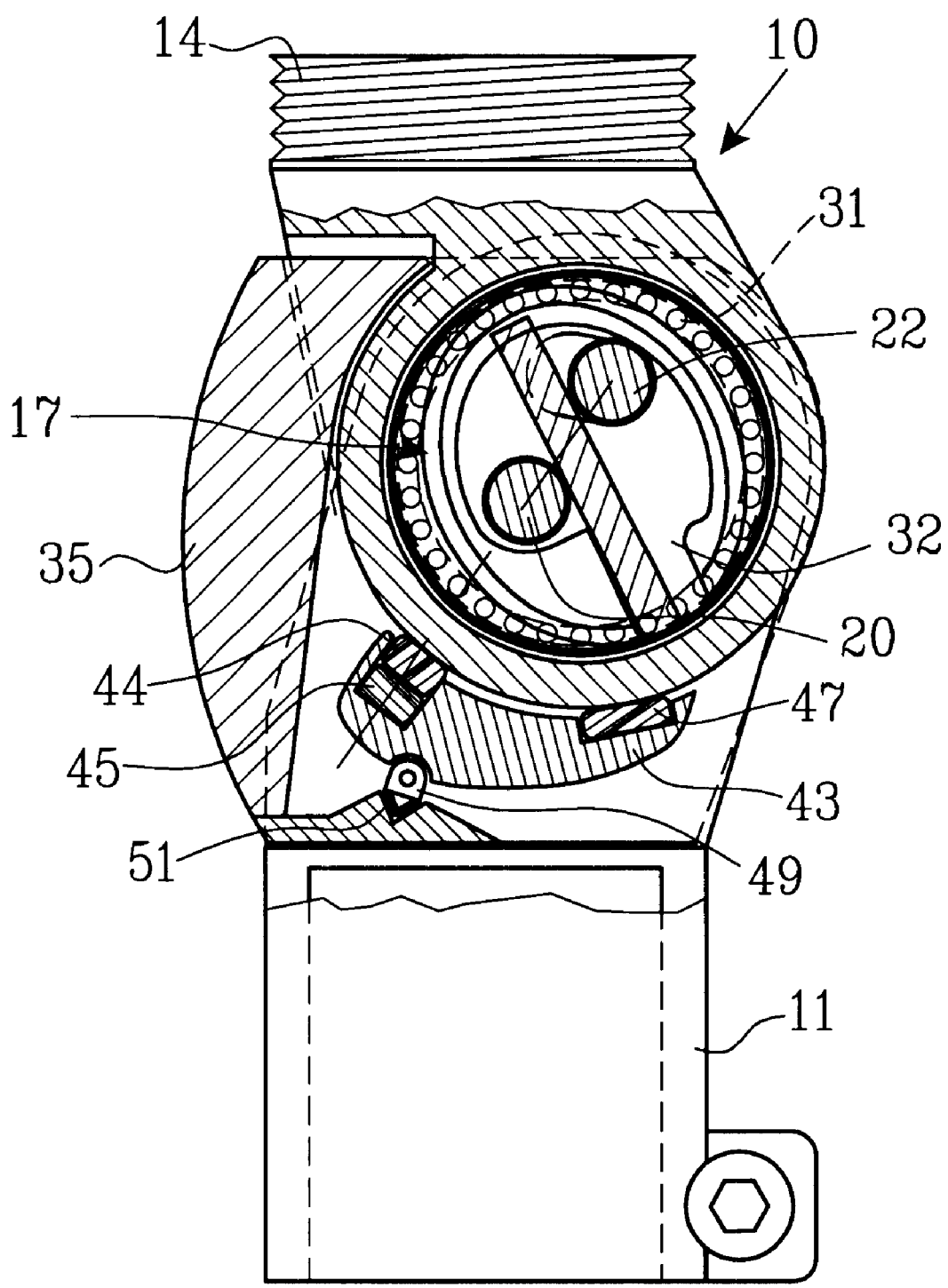
FIG. 14 is a longitudinal section through seventh embodiment of the knee prosthesis.
Figure 15:
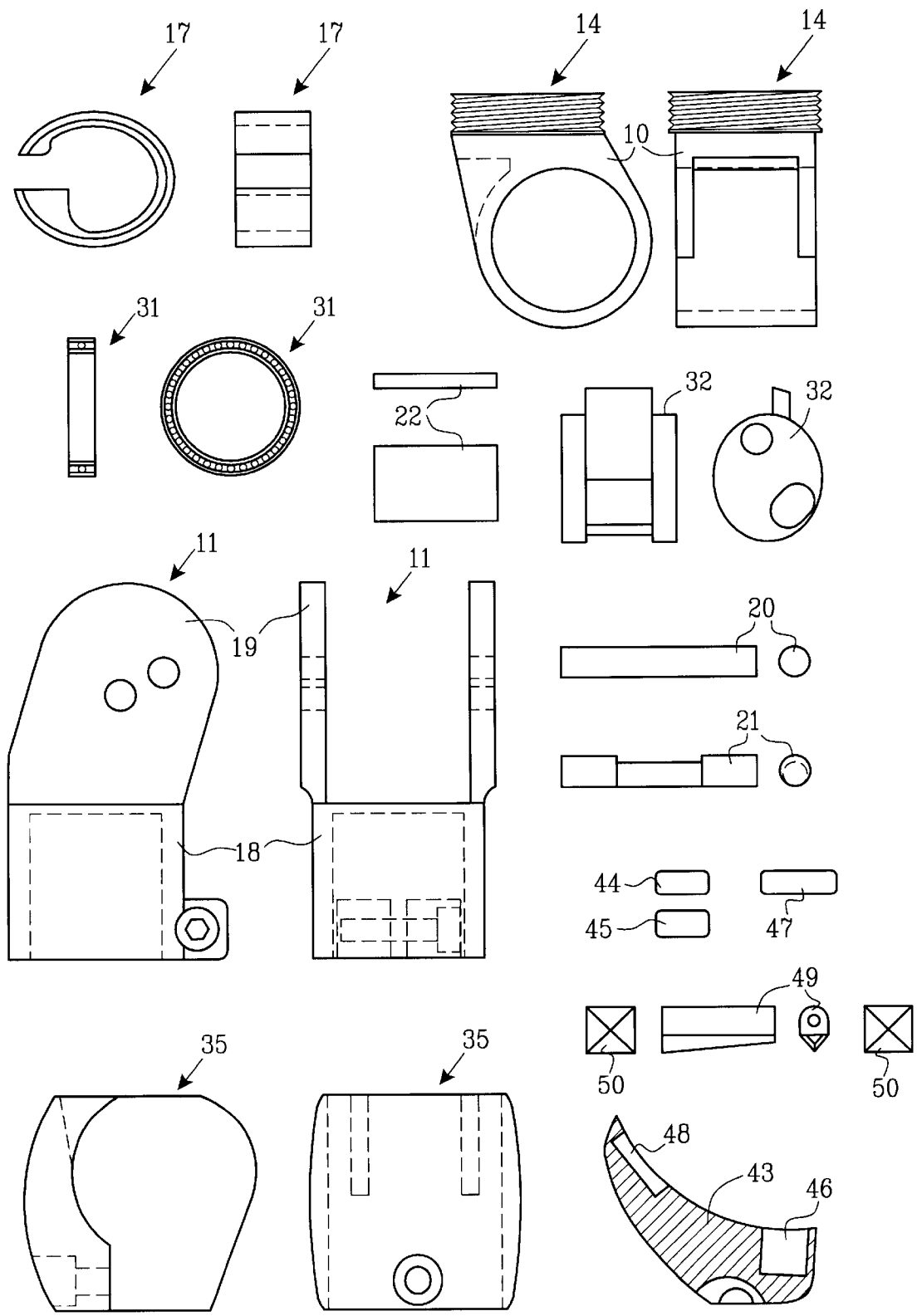
FIG. 15 is an exploded view of the knee prosthesis according to FIG. 14.

The embodiment according to FIGS. 14 and 15 is similar to the one disclosed in FIGS. 8–10 However the construction of the brake shoe 17 and of the plates 32 differ. The plates 32 which are provided with holes 33 and 34 for the axles 20 and 21 are interconnected by an intermediate member 32' around which the brake shoe 17 is arranged. The brake shoe 17 in this case h as no hole for the axle 20.

There is an essential difference in the construction of the friction adjustment device, with which the friction resistance against rotation of the knee joint is adjusted. This device comprises, in this case, a brake shoe 43, which can be tightened against the part-cylindrical surface 10a of the upper knee joint member 10. A friction element 44 which rests against a resilient rubber element 45 is arranged in a first recess 46 in the brake shoe 43, while a sliding block 47, for example made of TEFLON, is placed in a second recess 48 at the opposite end of the brake shoe. The brake shoe 43 is so arranged with respect to the axles 20 and 21 that the friction element will press against the knee joint member 10 at a point just opposite the axle 20 and its connection line with the axle 21. By this the important advantage is obtained that the friction in the knee joint can be adjusted without in a corresponding way influencing the function of the locking mechanism, i e the axle 21, the lever arm 22 and the brake shoe 17.

The friction adjusting device further includes a conical adjusting member 49, which by means of adjusting screws 50 can be displaced in a wedge-shaped groove 51 in the housing portion 35. By displacing the adjusting member 49 in the groove 51 the contact pressure of the friction element 44 against the knee joint member 10 is increased or decreased. In the shown embodiment the distance between the adjusting member 49 and the friction element 44 is about one third of the distance between the adjusting member 49 and the sliding block 47. This means that when a lifting force is applied on the adjusting member 49 by displacing this in its groove 51, this lifting force will be distributed so that 75% will be applied on the friction element 44 and 25% on the sliding block 47. The part of the lifting force from the adjusting member 49 which will be applied on the sliding block 47 is used for creating an upwards directed lifting force on the knee joint member 10. By this an unintentional locking of the brake shoe is prevented 10.

By this arrangement there is required a smaller force at heel strike for activating the brake shoe 17 as compared to the constructions shown above, where, for example, in FIG. 2, the entire expansion force from the element has to be overcome in order to get the brake to lock. The same thing applies also to FIG. 8 where the entire force from the resilient element has to be overcome before the brake locks. In the embodiment according to FIG. 14 there is only required that the lifting force from the sliding block 47 is overcome, said force amounts only to 25% of the total lifting force applied on the knee joint member 10 by means of the adjusting member 49, the brake shoe 43 and the friction elements 44 and 47.

The above described principle for friction adjustment of the rotation of the knee joint, where the frictional pressure applied on the knee joint member 10 just opposite the axle 20 and its imaginary connection line with the brake-activating axle 21, may of course be designed in different ways than shown in FIGS. 14 and 15, and can also be applied to the other embodiments. The advantage is disclosed above that the frictional resistance against the rotation of the knee joint acts and can be adjusted less dependant on the activation of the locking mechanism.

Figure 16:
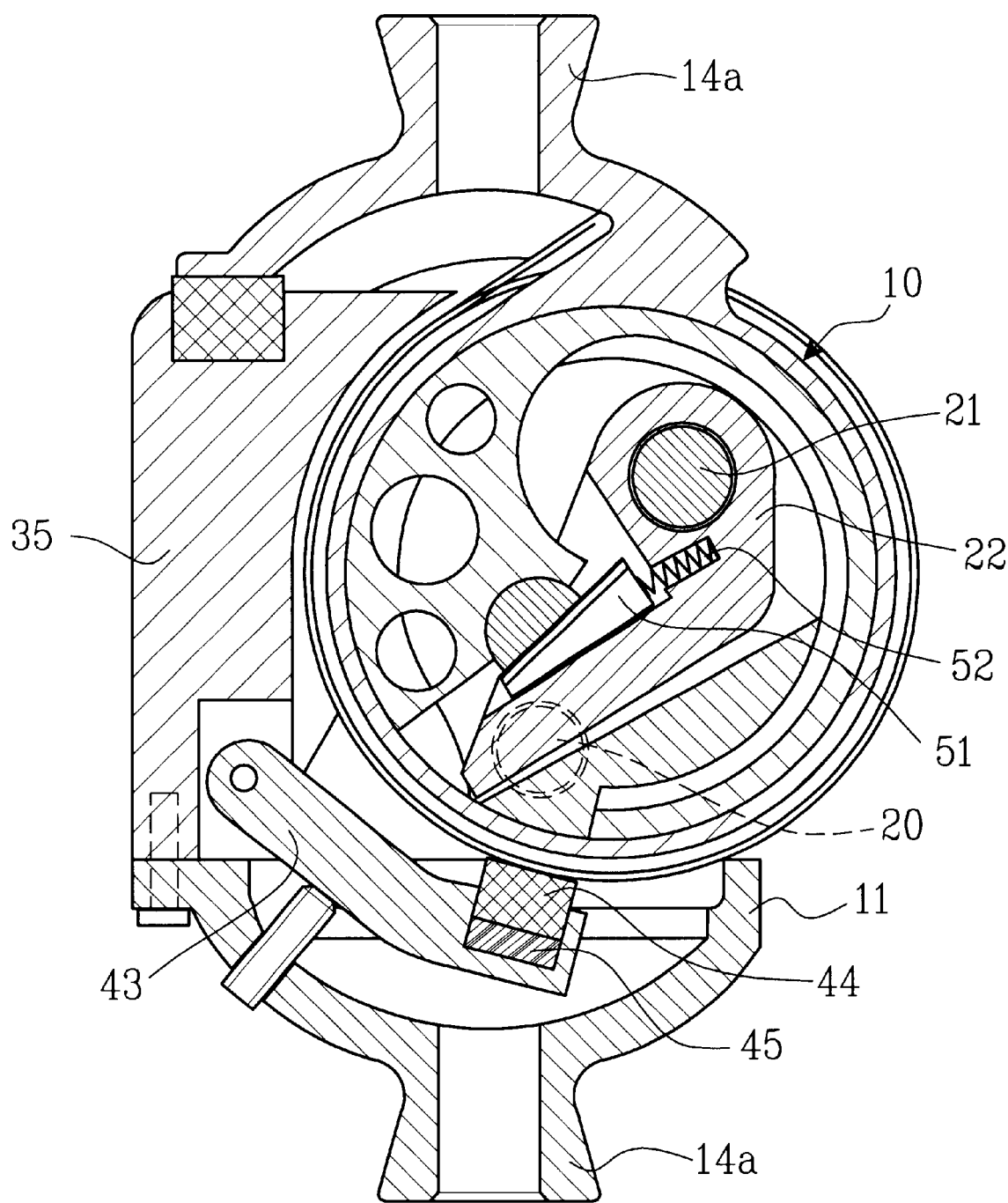
FIG. 16 is a longitudinal section through an eighth embodiment of the knee prosthesis.
Figure 17:
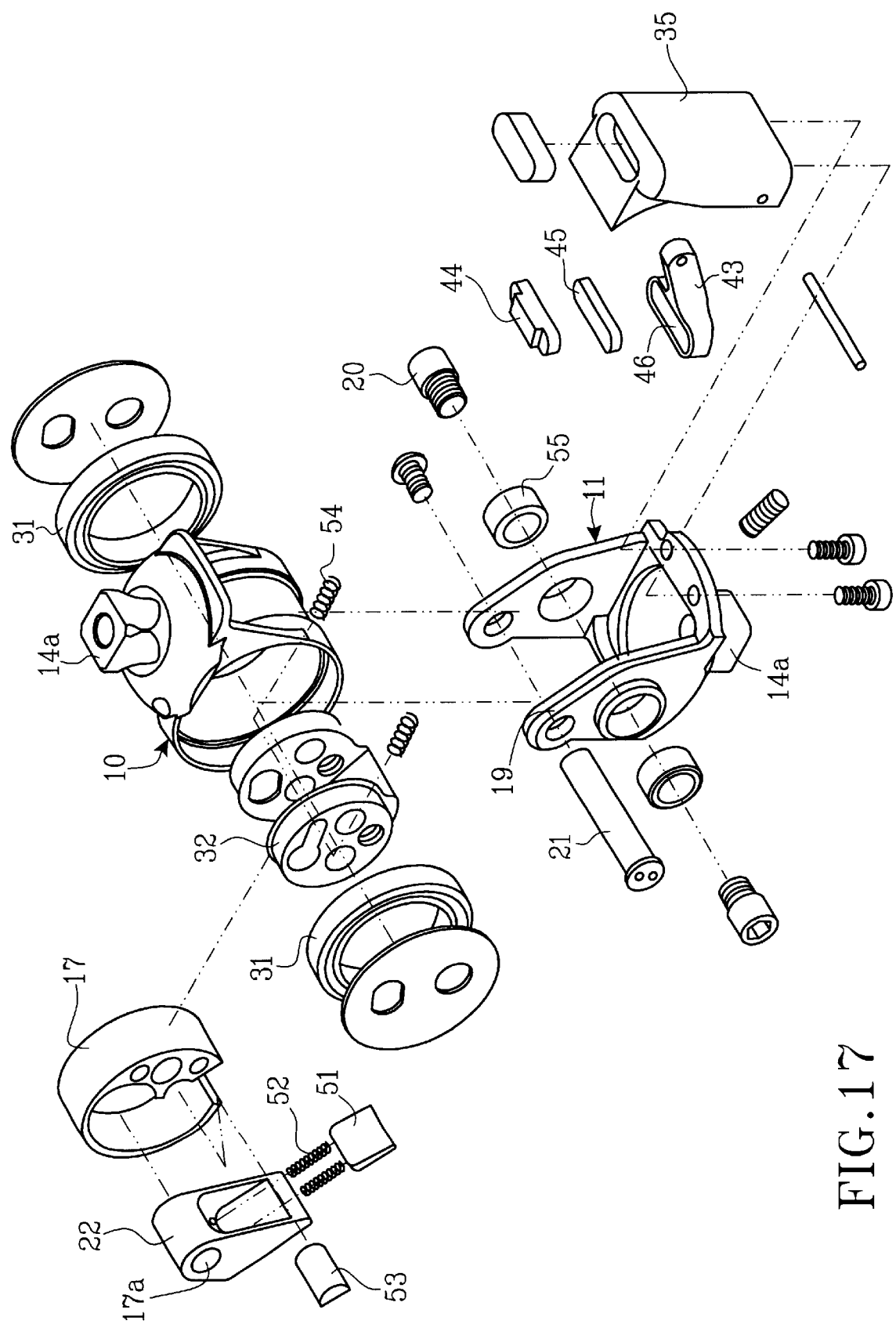
FIG. 17 is an exploded view of the knee prosthesis according to FIG. 16.
Figure 19:
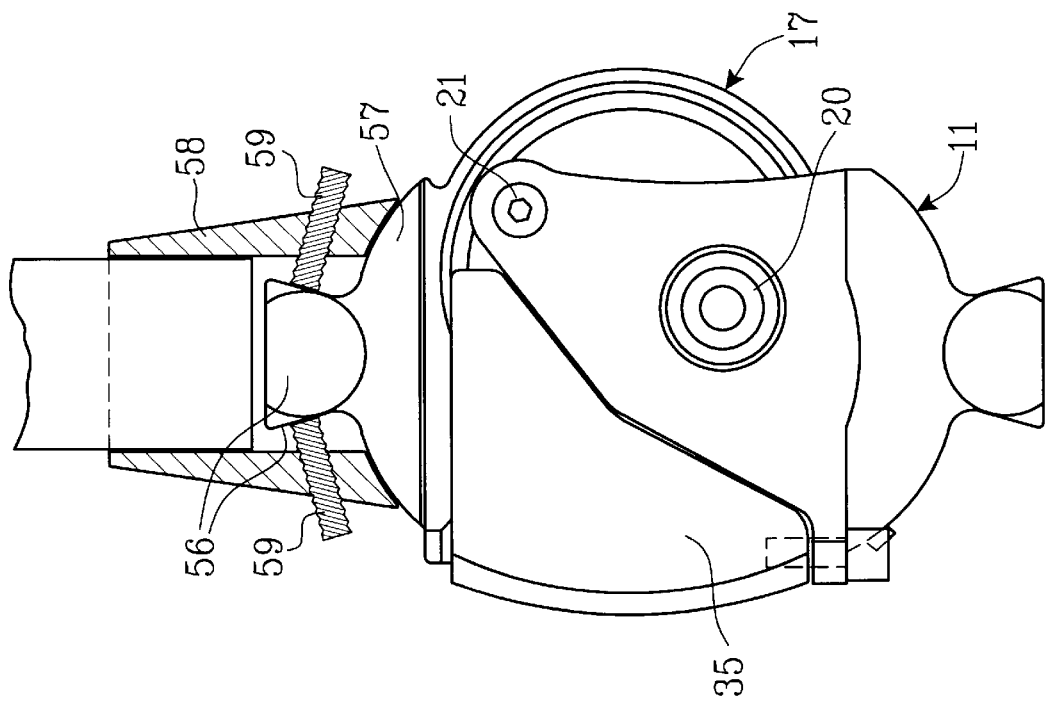
FIG. 19 is a side view of the knee prosthesis is according to FIGS. 16 and 17 and showing its attachment to a leg prosthesis.

The embodiment disclosed in FIGS. 16 and 17 is similar to the one according to FIGS. 14 and 15. The brake activating lever arm 22 however has a different design and is provided with an opening 17a through which the second brake activating axle 21 extends. The lever arm 22 is further provided with an automatic wear adjustment means in the form of a spring-loaded wedge 51. As the brake shoe 17 is worn on the outside the gap between its shanks is increased. The wedge 51 is then by the springs 52 pressed further into the gap between said shanks, so that there will not be needed a stronger force to activate the brake function. The numeral 53 denotes a member applied in a recess in the brake shoe and arranged to provide a contact surface for the wedge 51.

A pair of springs 54 provides a resilient element for lifting the brake activating axle 21. The springs 54 prevent the knee joint from self-locking and only lock in brake activated position. The springs 54 may be regarded to replace the resilient element 38 in FIGS. 8–10.

The first bearing axle 20 in this embodiment is shorter than in the previous embodiment. In FIG. 17, the numeral 55 denotes needle bearings.

The friction adjustment device, with which the friction resistance against rotation of the knee joint is adjusted is similar to the one disclosed in FIGS. 14–15 and comprises a brake arm 43, which can be tightened against the part-cylindrical surface 10a of the upper knee joint member 10. A friction element 44 rests against a resilient rubber element 45 is arranged in a recess 46 in the brake arm 43. The brake shoe 43 is so arranged with respect to the axles 20 and 21 that the friction element 44 will press against the knee joint member 10 at a point just opposite the axle 20 and its connection line with the axle 21. By this the important advantage is obtained that the friction in the knee joint can be adjusted without in a corresponding way influencing the function of the locking mechanism, i.e. the axle 21, the lever arm 22 and the brake shoe 17. The brake aim 43 is connected to a housing portion 35.

Figure 18A:
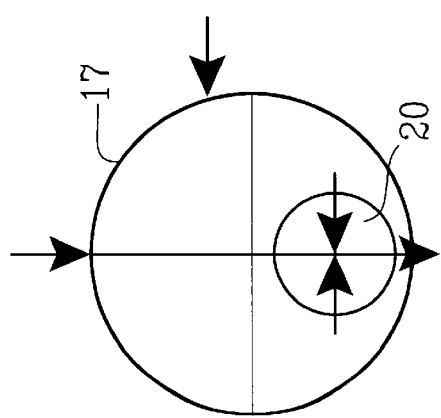
FIGS. 18a and b are schematic views illustrating the principle of function of the knee prosthesis.

The principal of the function of the braking system for the knee joint is schematically illustrated in FIGS. 18a and b. The principle for the geometric sensitivity of the braking device is that the internal rotatable cylindrical parts, including the brake shoe 17 and interconnected plates 32, is rotatably mounted in a rotary point, i.e. the first axle 20, placed out of centre position with respect to said internal rotatable cylindrical parts 17, 32. When as illustrated in FIG. 18a the knee joint is loaded so that the line of action of the load passes through the center of the internal cylindrical parts 17, 32 and the centre of the rotary point, i,e, first axle 20, the internal cylindrical part will be in balance and nothing will happen. This means that the brake is not activated.

Figure 18B:
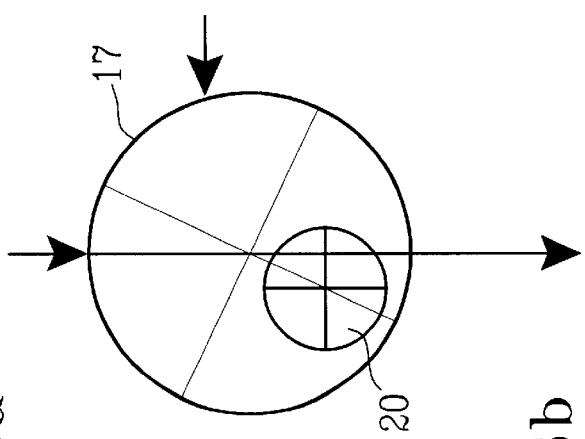

If however as illustrated in FIG. 18b the knee joint is loaded so that the line of action of the load passes out of center of the internal cylindrical parts 17, 32 and the centre of the rotary point, i e first axle 20, the cylindrical part will be out of balance and cannot hold the load without creating a rotary motion, which is used to activate the brake.

This geometric sensitivity of the braking device can, in combination with an angularly adjustable upper and lower connection to artificial leg member or prosthesis sleeve, be utilized to adjust the knee joint so that it locks (brakes) and unlocks respectively in different phases of the walking cycle. An example of such an angularly adjustable connection is a frustopyramidal socket 56 disclosed in FIGS. 16, 17, 19 and 20.

The connection means comprises a male part having a spherically convex base 57 from which a substantially frustopyramidal boss 56 rises divergently within an annular socket 58 constituting the female part and to which an artificial leg member 58 is connected. The frustopyramidal boss 56 is preferably four-sided and has two pairs of contact surfaces represented by the respective sides of the frustopyramid. The annular socket 58 is provided with four adjustable abutment means in the form of setscrews 59 engaging the contact surfaces of the boss 5 for retaining the two parts in a selected angular position within predetermined swing ranges in these two parts.

By adjusting the angular position of the knee joint with respect to the upper and lower leg prostheses the geometrical balance of the knee joint is adjusted. By this the brake system is activated and released in different phases of the walking cycle. The normal position is to have the brake activated during heel strike and mid stance, but released during toe off as explained above. Some prosthesis wearers having a high demand of mobility, for example for performing sports, however prefer a less stable knee joint which locks only at heel strike and unlocks already at mid-stance. Other prosthesis wearer prefers a more stable knee joint which remains locked through heel strike, mid-stance and toe load.

Figure 20A:
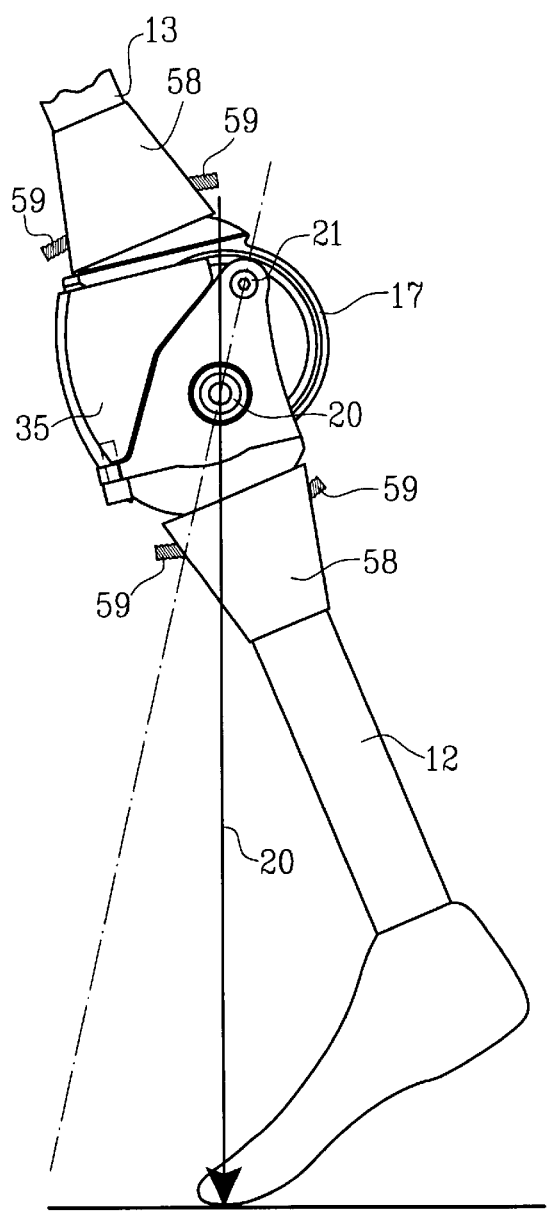
FIGS. 20a and b show in a toe off position the knee prosthesis according to FIG. 19 connected to upper and lower leg prosthesis in two different angularly adjusted positions.
Figure 20B:
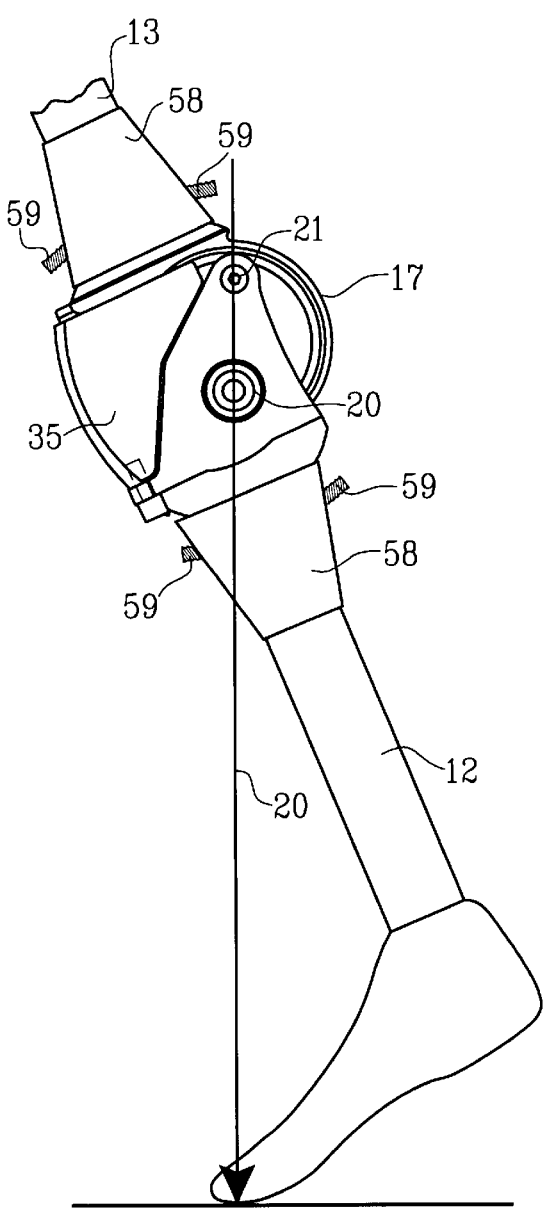

This is illustrated in FIGS. 20a and b, where FIG. 20a shows a position where the knee joint has been tilted backward as compared to the "normal" position shown in FIG. 20b. With the knee joint tilted to the position shown in FIG. 20a the brake will be activated at the toe load position shown, because the body weight line 26 will pass through the knee joint outside the centre of the rotating inner parts 17, 32 of the knee joint and their rotation axle 20. The knee joint will be out of balance and cannot hold the load without creating a rotary motion, which is used to activate the brake. With dotted lines is shown the imaginary angle of the load line needed for reaching the balanced position of the knee joint in which the brake is not activated. The knee joint remains thus locked during the entire walking phase from heel strike, mid-stance to toe off and is only released when there is no load on it.

In FIG. 20b is shown the "normal" position of the knee joint in which the brake is not activated in toe load position, since the body weight line 26 will pass through the geometrical centre of the rotating inner parts 17, 32 of the knee joint and through the rotation axle 20. However the knee joint will be locked at heel strike and mid-stance.

In a corresponding manner by tilting the joint forwards with respect to the "normal" position shown in FIG. 20b, the knee joint can be made less stable, for example so that it releases already at mid-stance and locks only at heel strike.

All described embodiments have a freewheel effect in such away that the knee joint can always rotate from flexed to extended position also under load. By this, for example, walking on stairs will be possible. The knee-joint will however lock immediately again if it is rotated in the opposite direction, for example from the extended to the flexed position, under such load that the locking device is activated.

The invention is of course not limited to the embodiments shown in the drawings but can be modified within the scope of the following claims. It applies for example for all embodiments that the coupling means to the prosthesis sleeve and to the lower leg can be of another type than described herein.

What is claimed is:

1. A knee joint for a prosthetic device, the knee joint comprising:

an upper knee joint member;

a lower knee joint member;

a bearing axle and a brake activating axle connecting the upper knee joint member to the lower knee joint member;

means for braking rotatably mounted to the bearing axle such that the axis of rotation of the braking means is off-center with respect to the axis of rotation of the said bearing axle, the means for braking comprising a brake activating axle and a locking device, the braking means including an activating member adapted to interact with the brake activating axle;

wherein the relative positions of the brake activating axle and the bearing axle is such as to create a geometric sensitivity of the rotating means for braking so that depending on the direction of a line of action from a load on the knee prosthesis the rotating means for braking will either be in balance at which the locking device is inactivated or out of balance at which the locking device is activated.

2. The knee joint of claim 1 further comprising:

a pair of interconnected plates defining an axial center, the pair of interconnected plates rotatably mounted on the bearing axle within the upper knee joint member such that the axis of rotation of the pair of interconnected plates is off-center with respect to the axial center;

a brake shoe retained between the pair of interconnected plates;

a brake arm rotatably connected to the lower knee joint member;

a brake activating lever arm rotatably retained on the brake activating axle and rotatably connected to the pair of interconnected plates, the brake activating lever arm adapted to activate the brake arm to engage the brake shoe; and a plurality of springs connected to the brake activating lever arm and adapted to lift the brake activating lever arm away from the brake shoe.

3. The knee joint of claim 1 further comprising an upper socket attached to the upper knee joint member adapted for connection to a prosthesis sleeve and a lower socket attached to the lower knee joint member adapted for connection to a lower leg prosthesis.

4. The knee joint of claim 3 wherein the upper socket and the lower socket each include angularly adjustable connection means.

5. The knee joint of claim 4 wherein the angularly adjustable connection means includes a frustopyramidal socket.

6. The knee joint of claim 1 further comprising means for wear adjustment, the wear adjustment means attached to the brake activating lever arm.

7. The knee joint of claim 6 wherein the wear adjustment means comprises a spring-loaded wedge.

8. A knee prosthesis comprising two pivotally interconnected members carrying a locking device and a bearing axle for the locking device and a brake activating axle forming an activation mechanism of the locking device;

wherein the interconnected members pivot about the locking device and the bearing and brake activating axles thereof and the locking device is arranged to permit the interconnected members to pivot in an unloaded position but prevent pivoting from extended to bent position when loaded;

wherein the relative positions of the brake activating axle and the bearing axle is such as to create a geometric sensitivity of the rotating means for braking so that depending on the direction of a line of action from a load on the knee prosthesis the rotating means for braking will either be in balance at which the locking device is inactivated or out of balance at which the locking device is activated;

wherein the locking device comprises a friction lock in the form of a brake drum or a brake clamp, which by means of the bearing axle is pivotally connected to one of the interconnected members and which cooperates with the brake activating axle in such a way that when the brake activating axle is loaded the locking device will frictionally lock to the other interconnected member, at which both interconnected members will lock to each other, while when the brake activating axle is unloaded they can be rotated with respect to each other; and wherein the brake activating axle cooperates with a lever arm which activated the brake drum or brake clamp against the action of a resilient element arranged between the brake drum or brake clamp and the lever arm on the opposite side thereof with respect to the brake activating axle.

9. The knee prosthesis according to claim 8, wherein the resilient element is adjustable for adapting to the body weight of a prosthesis wearer.

10. A knee prosthesis comprising two pivotally interconnected members carrying a locking device and a first and a second axle, the first axle forming a bearing axle for the locking device and the second axle forming an activation mechanism of the locking device;

wherein the interconnected members pivot about the locking device and the first and second axles thereof and the locking device is arrange to permit the members to pivot in an unloaded position but prevent pivoting from extended to bent position when loaded;

wherein the second axle is located at a distance behind the first axle and is arranged to act upon the locking device in such a way that when the line of action from a load on the knee prosthesis passes through the second axle or between the first and the second axle, the second axle will act upon the locking device to activate it, while when the line of action passes through the first axle or in front of it the second axle will be unloaded and the locking device inactivated at which the locking device comprises a friction lock in the form of a brake drum or a brake clamp, which by means of the first axle is pivotally connected to one of the knee prosthesis members and which cooperates with the second axle in such a way that when the second axle is loaded the locking device will frictionally lock to the second knee prosthesis member, at which both knee prosthesis members will lock to each other, while when the second axle is unloaded they can be rotated with respect to each other;

wherein the locking device comprises a brake drum or brake clamp, which by means of the first axle is pivotally connected to the upper knee prosthesis members and which cooperates with the second axle in such a way that when the second axle is loaded the brake drum or brake clamp will expand and frictionally lock within the lower knee prosthesis member designed as a bearing housing, at which two knee prosthesis members will lock to each other, while when the second axle is unloaded they can rotate with respect to each other;

wherein the relative positions of the first axle and the second axle is such as to create a geometric sensitivity of the rotating means for braking so that depending on the direction of a line of action from a load on the knee prosthesis the rotating means for braking will either be in balance at which the locking device is inactivated or out of balance at which the locking device is activated; and wherein the brake drum or brake clamp has the shape of an open ring and that a lever arm extends between a first and second shanks forming the opening of the open ring and to activation of the brake drum or brake clamp forces said shanks apart.

11. A knee prosthesis comprising two pivotally interconnected members carrying a locking device and a first and a second axle, the first axle forming a bearing axle for the locking device and the second axle forming an activation mechanism of the locking device, wherein the interconnected members pivot about the first axle and the locking device is arranged to permit the members to pivot in an unloaded position but prevent pivoting from extended to bent position when loaded;

wherein the second axle is located at a distance behind the first axle and is arranged to act upon the locking device in such a way that when the line of action from a load on the knee prosthesis passes through the second axle or between the first and the second axle, the second axle will act upon the locking device activate it, while when the line of action passes through the first axle or in front of it the second axle will be unloaded and the locking device inactivated at which the locking device comprises a friction lock in the form of a brake drum or brake clamp, which by means of the first axle is pivotally connected to one of the knee prosthesis members and which cooperates with the second axle in such a way that when the second axle is loaded the locking device will frictionally lock to the second knee prosthesis member, at which both knee prosthesis members will lock to each other, while when the second axle is unloaded they can be rotated with respect to each other;

wherein the brake drum or brake clamp, which by means of the first axle is pivotally connected to the upper knee prosthesis members and which cooperates with the second axle in such a way that when the second axle is loaded, will expand and frictionally lock within the lower knee prosthesis member designed as a bearing house, at which the two knee prosthesis members will lock to each other, while when the second axle is unloaded they can rotate with respect to each other;

wherein the relative position of the first axle and the second axle is such as to create a geometric sensitivity of the rotating means for braking so that depending on the direction of a line of action from a load on the knee prosthesis the rotating means for braking will either be in balance at which the device inactivated or out of balance at which the locking device is activated; and wherein the locking device a comprises a brake drum or brake clamp is in the form of an open ring one end surface of which cooperates with the second axle.

* * * * *